(12) United States Patent
Lee et al.

(10) Patent No.: US 12,721,530 B2
(45) Date of Patent: Sep. 1, 2026

(54) MULTI-CHANNEL BLOOD VISCOSITY MEASURING DEVICE

(71) Applicant: BIORHEOLOGICS CO., LTD., Jeonju-si (KR)

(72) Inventors: Dong Hwan Lee, Jeonju-si (KR); Dal Sik Kim, Jeonju-si (KR); Ui Yun Lee, Jeonju-si (KR); Eui Ho Lee, Hwaseong-si (KR)

(73) Assignee: BIORHEOLOGICS CO., LTD., Jeonju-si (KR)

( * ) Notice: Subject to any disclaimer, the term of this patent is extended or adjusted under 35 U.S.C. 154(b) by 580 days.

(21) Appl. No.: 18/021,349

(22) PCT Filed: Aug. 19, 2021

(86) PCT No.: PCT/KR2021/011010

§ 371 (c)(1),
(2) Date: Feb. 14, 2023

(87) PCT Pub. No.: WO2022/039512

PCT Pub. Date: Feb. 24, 2022

(65) Prior Publication Data

US 2023/0320595 A1 Oct. 12, 2023

(30) Foreign Application Priority Data

Aug. 19, 2020 (KR) ........................ 10-2020-0104136

(51) Int. Cl.
*A61B 5/02* (2006.01)
*G01N 11/04* (2006.01)
(Continued)

(52) U.S. Cl.
CPC .......... *A61B 5/02035* (2013.01); *G01N 11/04* (2013.01); *G01N 35/10* (2013.01); *G01N 2035/00524* (2013.01)

(58) Field of Classification Search
CPC .... A61B 5/02035; G01N 11/04; G01N 35/10; G01N 2035/00524; G01N 33/49; G01N 35/04
See application file for complete search history.

(56) References Cited

U.S. PATENT DOCUMENTS

2015/0177236 A1 6/2015 Van Praet et al.
2025/0209836 A1 * 6/2025 Moon .................. G06V 20/693

FOREIGN PATENT DOCUMENTS

CN 103988064 A 8/2014
EP 0608425 B1 * 6/1997 ............. G01N 33/49
(Continued)

OTHER PUBLICATIONS

KR 10-1476923 B1 with English translation (Year: 2014).*

*Primary Examiner* — Jeffrey G. Hoekstra
(74) *Attorney, Agent, or Firm* — Bridgeway IP Law Group, PLLC; Sang Ho Lee; Hyun Woo Shin

(57) ABSTRACT

Provided is a multi-channel blood viscosity measuring device including: a blood sample preprocessing unit for scanning and shaking a blood collection tube and then removing a blood collection tube cover therefrom; a blood sample transfer unit for moving the blood collection tube stably placed by the blood sample preprocessing unit; a blood viscosity measuring unit including one or more channels and equipped with a blood viscosity measuring kit to measure the viscosity of an injected blood sample; and a blood sample post-processing unit for mounting the blood viscosity measuring kit on the blood viscosity measuring unit and suctioning the blood sample from the blood collection tube transferred by the blood sample transfer unit to inject same into the mounted blood viscosity measuring kit.

20 Claims, 20 Drawing Sheets

(51) Int. Cl.
*G01N 35/00* (2006.01)
*G01N 35/10* (2006.01)

(56) References Cited

FOREIGN PATENT DOCUMENTS

| | | | | | |
|---|---|---|---|---|---|
| KR | 10-0958447 | B1 | | 5/2010 | |
| KR | 10-1221786 | B1 | | 1/2013 | |
| KR | 10-2013-0107146 | A | | 10/2013 | |
| KR | 20130107146 | A | * | 10/2013 | ......... G01N 35/1081 |
| KR | 10-1476923 | B1 | | 12/2014 | |
| KR | 20170001768 | A | * | 1/2017 | ............. G01N 11/04 |
| KR | 10-2017-0127993 | A | | 11/2017 | |
| KR | 10-1910561 | B1 | | 10/2018 | |
| KR | 102822954 | B1 | * | 6/2025 | ......... G01N 35/1079 |
| WO | WO-2011119492 | A2 | * | 9/2011 | .............. A61P 31/00 |
| WO | 2013/036941 | A2 | | 3/2013 | |

* cited by examiner

MULTI-CHANNEL BLOOD VISCOSITY MEASURING DEVICE

TECHNICAL FIELD

The present invention relates to a multi-channel blood viscosity measuring device, and more particularly, to a multi-channel blood viscosity measuring device capable of automatically and simultaneously measuring the viscosity of one or more blood samples to uniformly measure the viscosity of the blood samples, thereby improving accuracy and reducing work time.

BACKGROUND ART

The viscosity of blood is a physical property representing flow resistance due to the flow of blood in a blood vessel and may be specifically divided into whole blood viscosity and plasma viscosity. An abnormal increase in blood viscosity causes an increase in shear stress and flow resistance acting on the inner walls of blood vessels, resulting in a significant increase in risk of developing acute cardiovascular disease and microvascular disease. In addition, plasma viscosity is used to diagnose inflammatory conditions in the body and is one of the main causes of increasing whole-blood viscosity.

Whole blood viscosity exhibits flow characteristics in which the viscosity continuously changes according to the systole and diastole of the heart. This is because the viscosity decreases when blood flows at high speed (when the shear rate is high) due to the mutually complex effects of red blood cells and plasma proteins in whole blood, and conversely, the viscosity increases when blood flows at a slow rate (when the shear rate is low). Fluids exhibiting these flow characteristics are called non-Newtonian fluids. In order to properly understand the non-Newtonian flow characteristics of blood, it is necessary to accurately measure the whole blood viscosity for the entire shear rate (e.g., 1 to 1,000 s^−1).

A recent blood viscosity measuring device allows blood obtained from the body to pass through a flow restrictor tube and measures the flow characteristics of the blood in the flow restrictor tube to measure blood viscosity or hemagglutination rate.

As the prior art, Korean Utility Model Registration No. 20-0331884 (Device for Simultaneously Measuring Blood Viscosity and Hemagglutination Rate) is disclosed.

However, since a device operator has to manually inject blood through a syringe and measure the viscosity of the blood, it is difficult to supply the blood at a constant pressure and a constant flow rate, making it difficult to measure the viscosity of the blood under the same conditions. In addition, there has been a problem that the manual work took a long time.

In addition, due to the manual work, infection by blood has frequently occurred.

In order to solve these problems, an automated blood viscosity measuring device is being developed. However, after the viscosity measurement of one blood sample is completed, the viscosity measurement of the next blood sample is performed, which takes a lot of work time.

In addition, upon measuring a large amount of blood samples, in the case of late blood samples, the viscosity of the blood is measured in a state in which red blood cells have settled over time, resulting in a problem of low viscosity measurement accuracy.

DISCLOSURE

Technical Problem

In order to solve the problems described above, the present invention aims to provide a multi-channel blood viscosity measuring device capable of automatically and simultaneously measuring the viscosity of one or more blood samples to uniformly measure the viscosity of the blood samples, thereby improving accuracy and reducing work time.

Technical Solution

In order to solve the above problems, a multi-channel blood viscosity measuring device, according to an embodiment of the present invention, may include: a blood sample preprocessing unit for scanning and shaking a blood collection tube and then removing a blood collection tube cover therefrom; a blood sample transfer unit for moving the blood collection tube stably placed by the blood sample preprocessing unit; a blood viscosity measuring unit including one or more channels and equipped with a blood viscosity measuring kit to measure a viscosity of an injected blood sample; and a blood sample post-processing unit for mounting the blood viscosity measuring kit on the blood viscosity measuring unit and suctioning the blood sample from the blood collection tube transferred by the blood sample transfer unit to inject the blood sample into the mounted blood viscosity measuring kit.

Here, the blood sample preprocessing unit may include: a preprocessing clamp unit capable of holding and rotating the blood collection tube; and a preprocessing position adjusting unit for adjusting a position of the preprocessing clamp unit.

In addition, the preprocessing clamp unit may include: a preprocessing clamp capable of holding or placing the blood collection tube; a first rotating unit capable of rotating the preprocessing clamp around z-axis, and a second rotating unit capable of rotating the preprocessing clamp around x-axis or y-axis.

In addition, the preprocessing position adjusting unit may include one or more of a preprocessing up-and-down adjusting unit capable of adjusting the position of the preprocessing clamp unit in an up-and-down direction, a preprocessing left-and-right adjusting unit capable of adjusting the position of the preprocessing clamp unit in a left-and-right direction, and a preprocessing front and rear adjusting unit capable of adjusting the position of the preprocessing clamp unit in a front and rear direction.

In addition, the blood sample transfer unit may include: a transfer clamp unit on which the blood collection tube is stably placed by the blood sample preprocessing unit; and a transfer unit connected to the transfer clamp unit to transfer the stably placed blood collection tube.

In addition, the channel of the blood viscosity measuring unit may include: a kit mounting member on which the blood viscosity measuring kit is mounted; a viscosity measuring unit into which the kit mounting member equipped with the blood viscosity measuring kit is inserted and which measures the viscosity of the blood sample injected into the blood viscosity measuring kit; and a kit inserting unit for inserting or withdrawing the kit mounting member into or from the viscosity measuring unit.

In addition, the blood sample post-processing unit may include: a kit clamp unit capable of holding or placing the blood viscosity measuring kit; a pipette unit for suctioning the blood sample from the blood collection tube equipped with a pipette tip and injecting the blood sample into the blood viscosity measuring kit; and a post-processing position adjusting unit for adjusting positions of the kit clamp unit and the pipette unit.

In addition, the post-processing position adjusting unit may include one or more of a post-processing up-and-down adjusting unit capable of adjusting positions of the kit clamp unit and the pipette unit in an up-and-down direction, a post-processing left-and-right adjusting unit capable of adjusting the position of the kit clamp unit and the pipette unit in a left-and-right direction, and a post-processing front and rear adjusting unit capable of adjusting the positions of the kit clamp unit and the pipette unit in a front and rear direction.

In addition, the post-processing up-and-down adjusting unit may include: a kit up-and-down adjusting unit connected to the kit clamp unit and capable of adjusting the position of the kit clamp unit in the up-and-down direction; and an integrated up-and-down adjusting unit connected to the kit up-and-down adjusting unit and the pipette unit to adjust the positions of the kit clamp unit and the pipette unit in the up-and-down direction.

In addition, the multi-channel blood viscosity measuring device may further include: a control unit for controlling operations of the blood sample preprocessing unit, the blood sample transfer unit, the blood viscosity measuring unit, and the blood sample post-processing unit; and a monitoring unit capable of monitoring a viscosity measurement result measured by the blood viscosity measuring unit.

In addition, the multi-channel blood viscosity measuring device may further include a blood sample mounting unit capable of mounting one or more blood collection tubes.

In addition, the multi-channel blood viscosity measuring device may further include a blood viscosity measurement cartridge for storing a blood viscosity measuring kit before use.

In addition, the multi-channel blood viscosity measuring device may further include a pipette tip storage unit for storing a pipette tip before use.

In addition, the multi-channel blood viscosity measuring device may further include a waste processing unit for accommodating a blood viscosity measuring kit for which the viscosity measurement of the blood sample has been completed in the blood viscosity measuring unit.

Advantageous Effects

A multi-channel blood viscosity measuring device according to an embodiment of the present invention is capable of automatically measuring the viscosity of blood samples accommodated in blood collection tubes without a separate operation by a device operator and discarding a waste kit after measuring the blood viscosity, whereby it may be efficient when blood samples are measured in large quantities.

In addition, since the viscosity of each blood sample is uniformly measured, the viscosity measurement accuracy of each blood sample may be improved.

In addition, since the viscosity measurement of one or more blood samples may be performed simultaneously, the work time may be further shortened.

BEST MODE FOR CARRYING OUT THE INVENTION

The present invention relates to a multi-channel blood viscosity measuring device. More specifically, the present invention may provide a multi-channel blood viscosity measuring device comprising: a blood sample preprocessing unit for scanning and shaking a blood collection tube and then removing a blood collection tube cover therefrom; a blood sample transfer unit for moving the blood collection tube stably placed by the blood sample preprocessing unit; a blood viscosity measuring unit including one or more channels and equipped with a blood viscosity measuring kit to measure the viscosity of an injected blood sample; and a blood sample post-processing unit for mounting the blood viscosity measuring kit on the blood viscosity measuring unit and suctioning the blood sample from the blood collection tube transferred by the blood sample transfer unit to inject same into the mounted blood viscosity measuring kit.

MODE FOR INVENTION

Hereinafter, the description of the present invention with reference to the drawings is not limited to specific embodiments, and various modifications may be made thereto, and various embodiments may be provided. In addition, the following description should be understood to include all changes, equivalents, or substitutes included in the spirit and scope of the present invention.

In the following description, the terms such as "first" and "second" are terms used to describe various elements, are not limited in meaning itself, and are only used to distinguish one element from another.

Like reference numbers used throughout the present specification represent like elements.

The singular forms, as used herein, are intended to include the plural forms as well unless the context clearly indicates otherwise. The terms "comprise," "include," and "have" as used herein are inclusive and therefore specify the presence of stated features, integers, steps, operations, elements, components, or combinations thereof, but do not preclude the presence or addition of one or more other features, integers, steps, operations, elements, components, or combinations thereof.

Hereinafter, an embodiment of the present invention will be described in detail with reference to FIGS. 1 to 20 attached herein.

Figure 1:
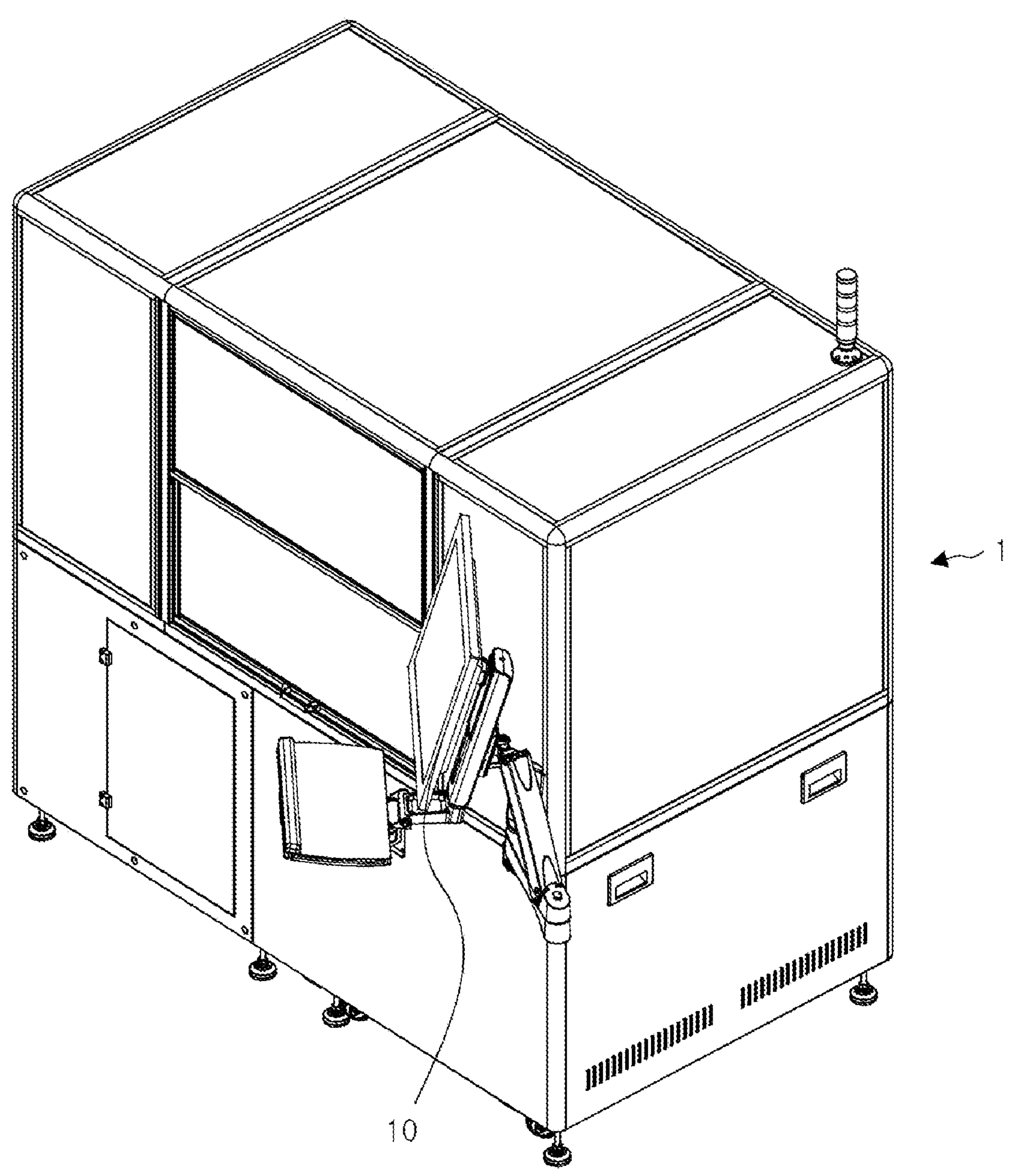
FIG. 1 is a perspective view illustrating a multi-channel blood viscosity measuring device according to an embodiment of the present invention.
Figure 2:
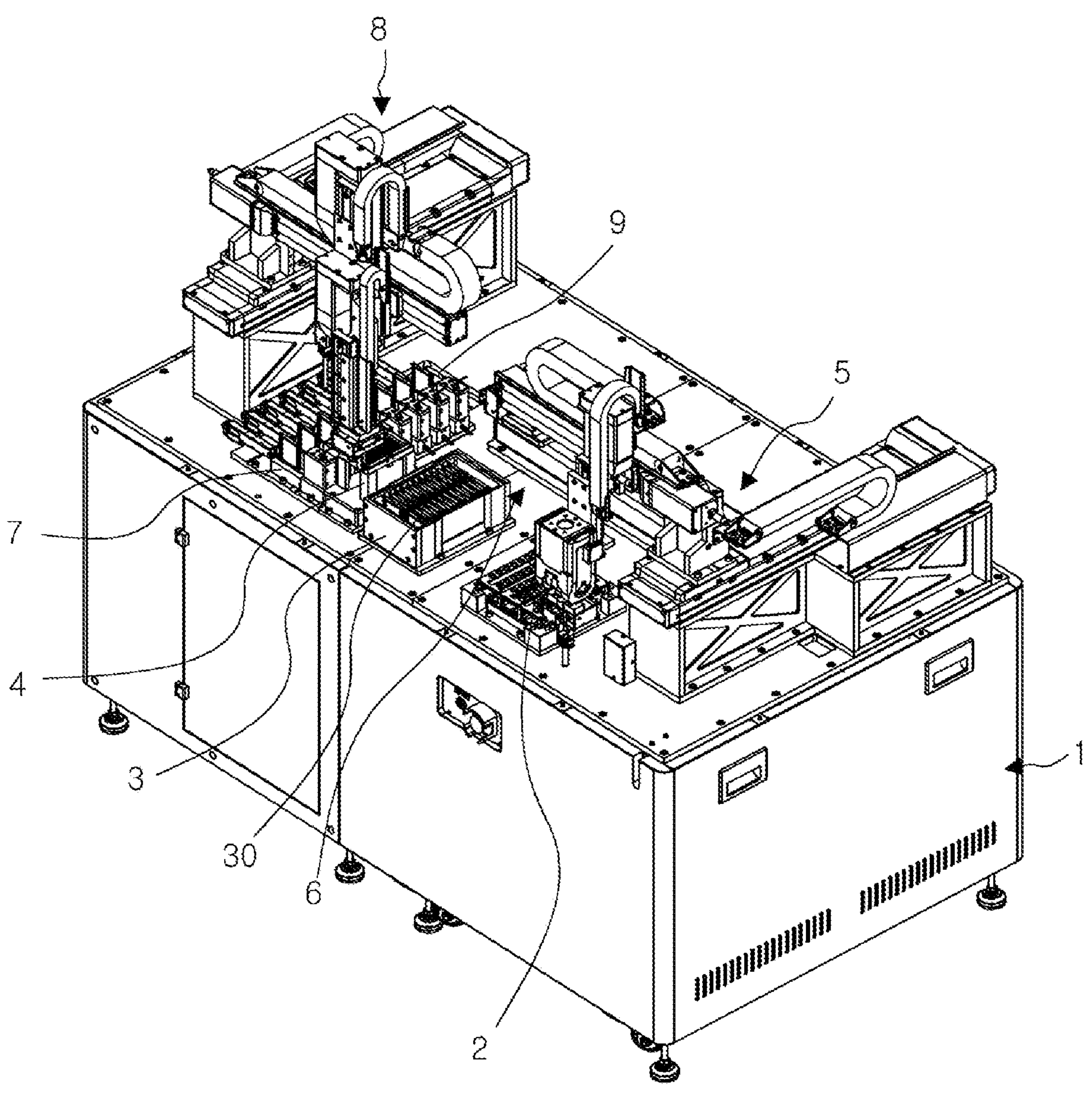
FIG. 2 is a perspective view illustrating the multi-channel blood viscosity measuring device, a portion of which is removed, according to an embodiment of the present invention.
Figure 3:
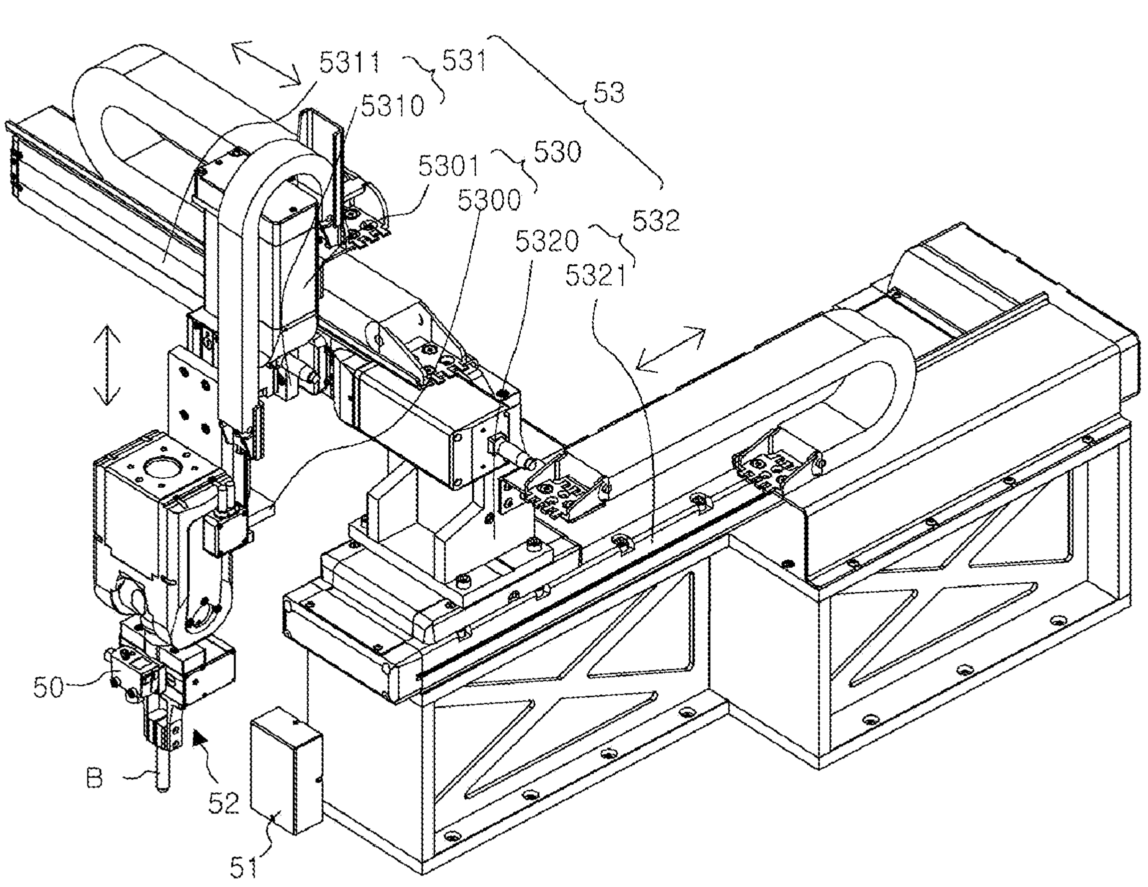
FIG. 3 is a perspective view illustrating a blood sample preprocessing unit of FIG. 2.
Figure 4:
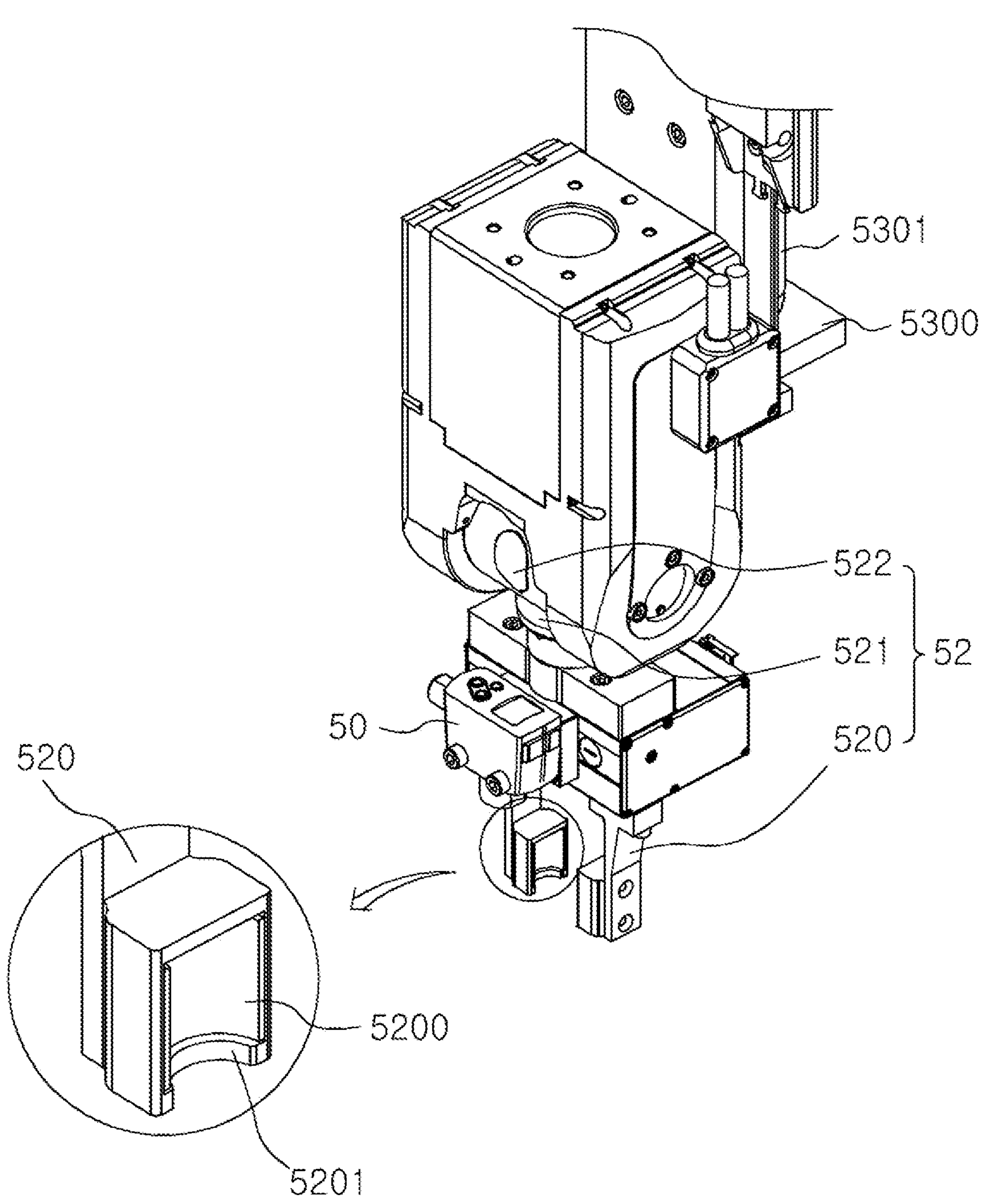
FIG. 4 is an enlarged perspective view of a preprocessing clamp unit of FIG. 3.
Figure 5A:
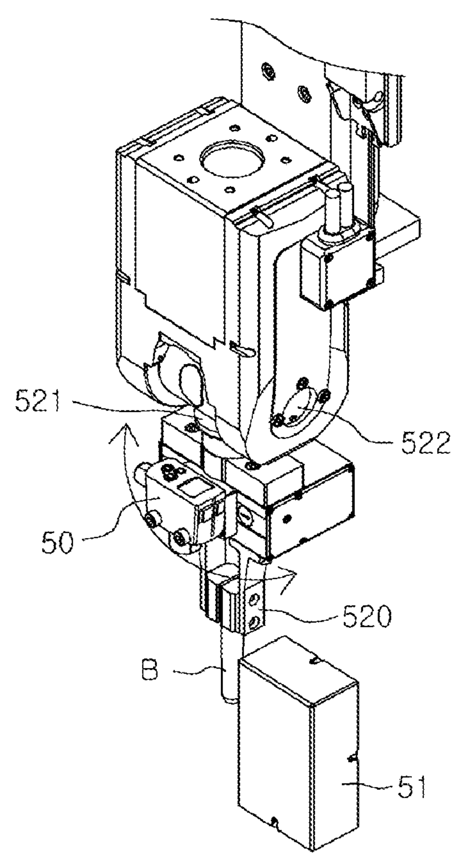
FIGS. 5(*a*) and 5(*b*) are exemplary operation diagrams illustrating a state in which the preprocessing clamp unit of the multi-channel blood viscosity measuring device is operated to scan and shake the blood collection tube, according to an embodiment of the present invention.
Figure 5A:
Figure 5B:
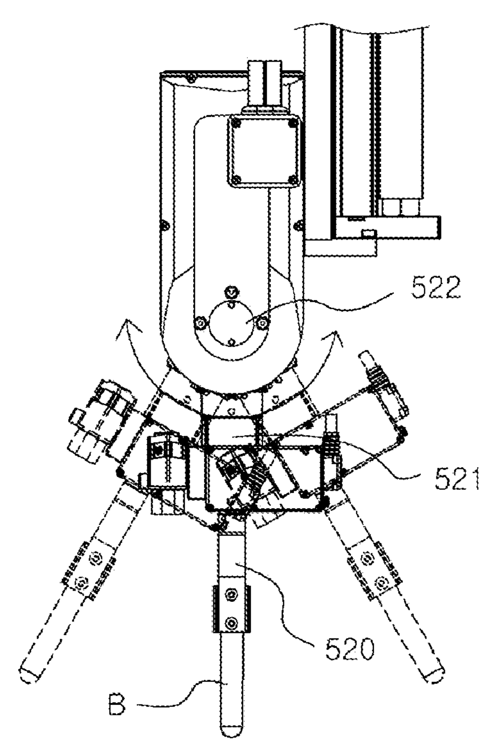
Figure 6:
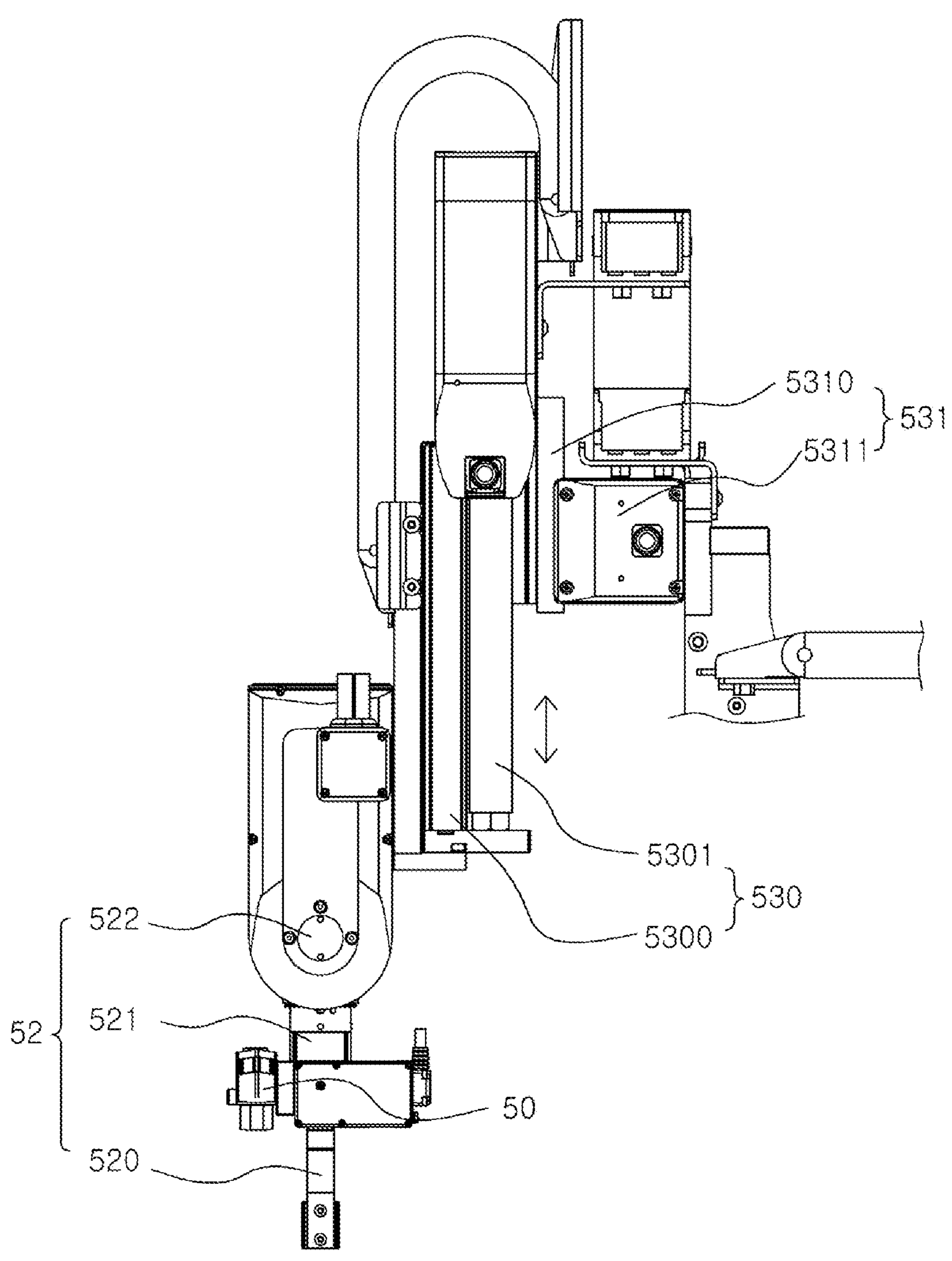
FIG. 6 is an enlarged side view of a preprocessing up-and-down adjusting unit of FIG. 3.
Figure 7:
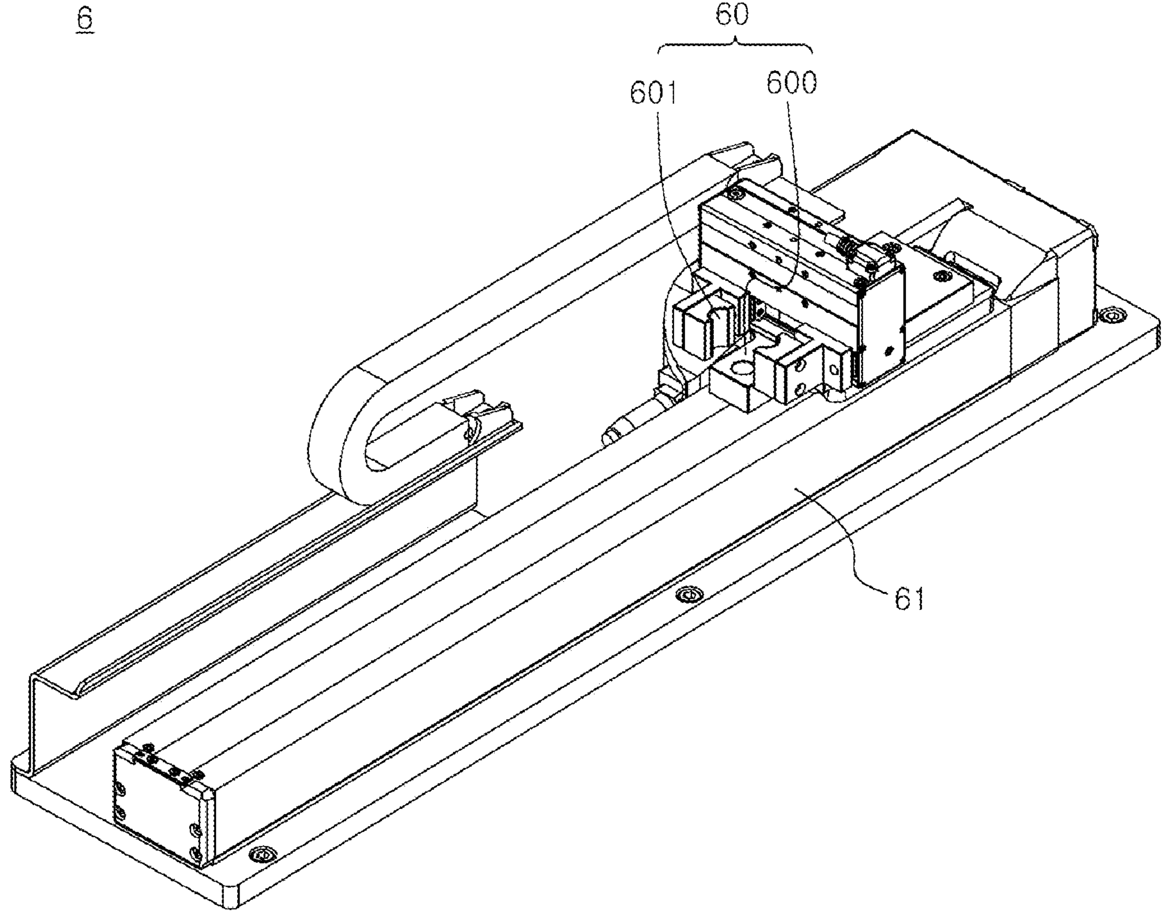
FIG. 7 is a rotational perspective view illustrating a blood sample transfer unit of FIG. 2.
Figure 8A:
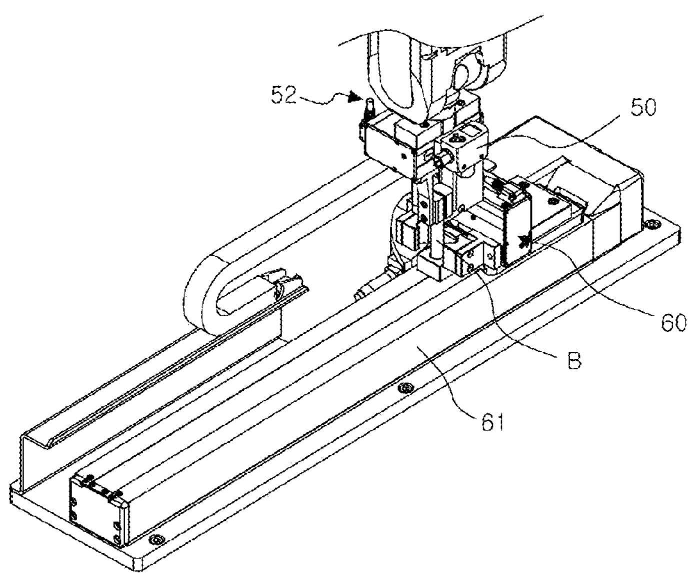
FIGS. 8(*a*) and 8(*b*) are exemplary diagrams illustrating a process of transferring the blood collection tube stably placed on the blood sample transfer unit of the multi-channel blood viscosity measuring device, according to an embodiment of the present invention.
Figure 8B:
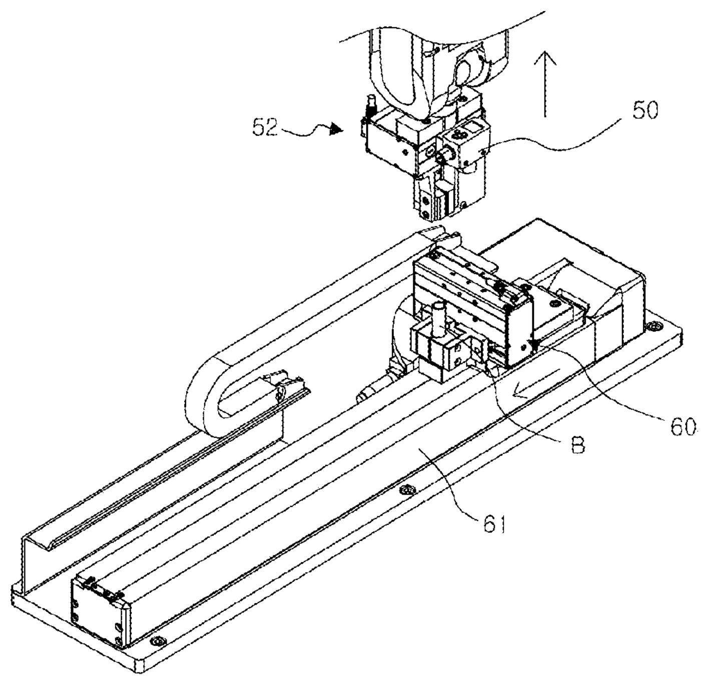
Figure 9:
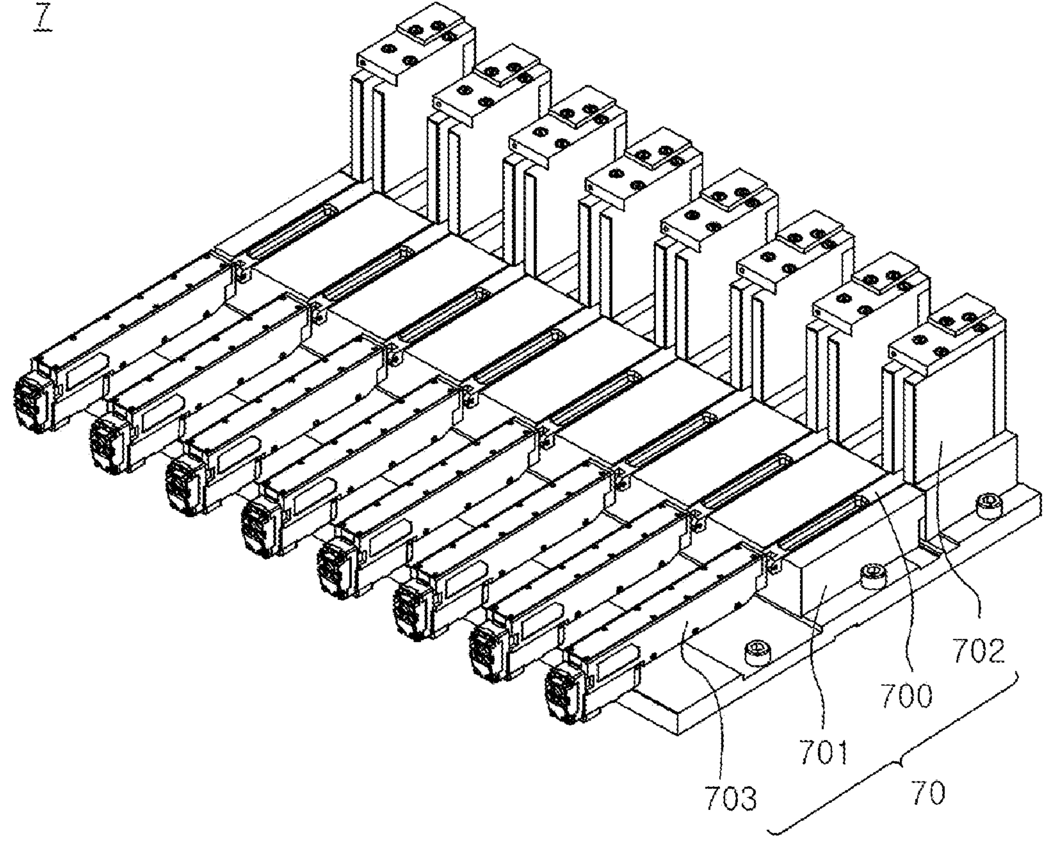
FIG. 9 is a rotational perspective view of a blood viscosity measuring unit of FIG. 2.
Figure 10A:
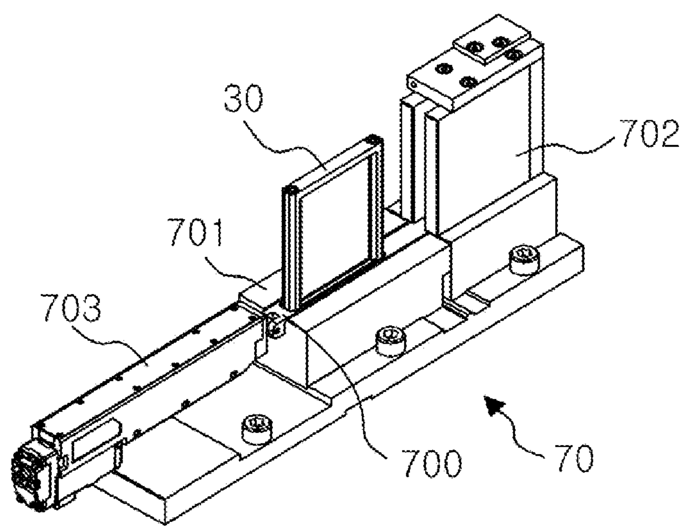
FIGS. 10(*a*) and 10(*b*) are exemplary operation diagrams illustrating a state in which a blood viscosity measuring kit is mounted and operated in the blood viscosity measuring unit of the multi-channel blood viscosity measuring device, according to an embodiment of the present invention.
Figure 10B:
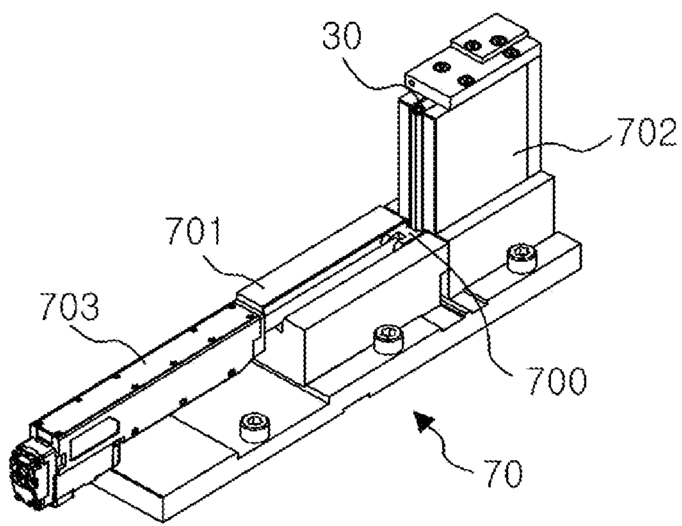
Figure 11:
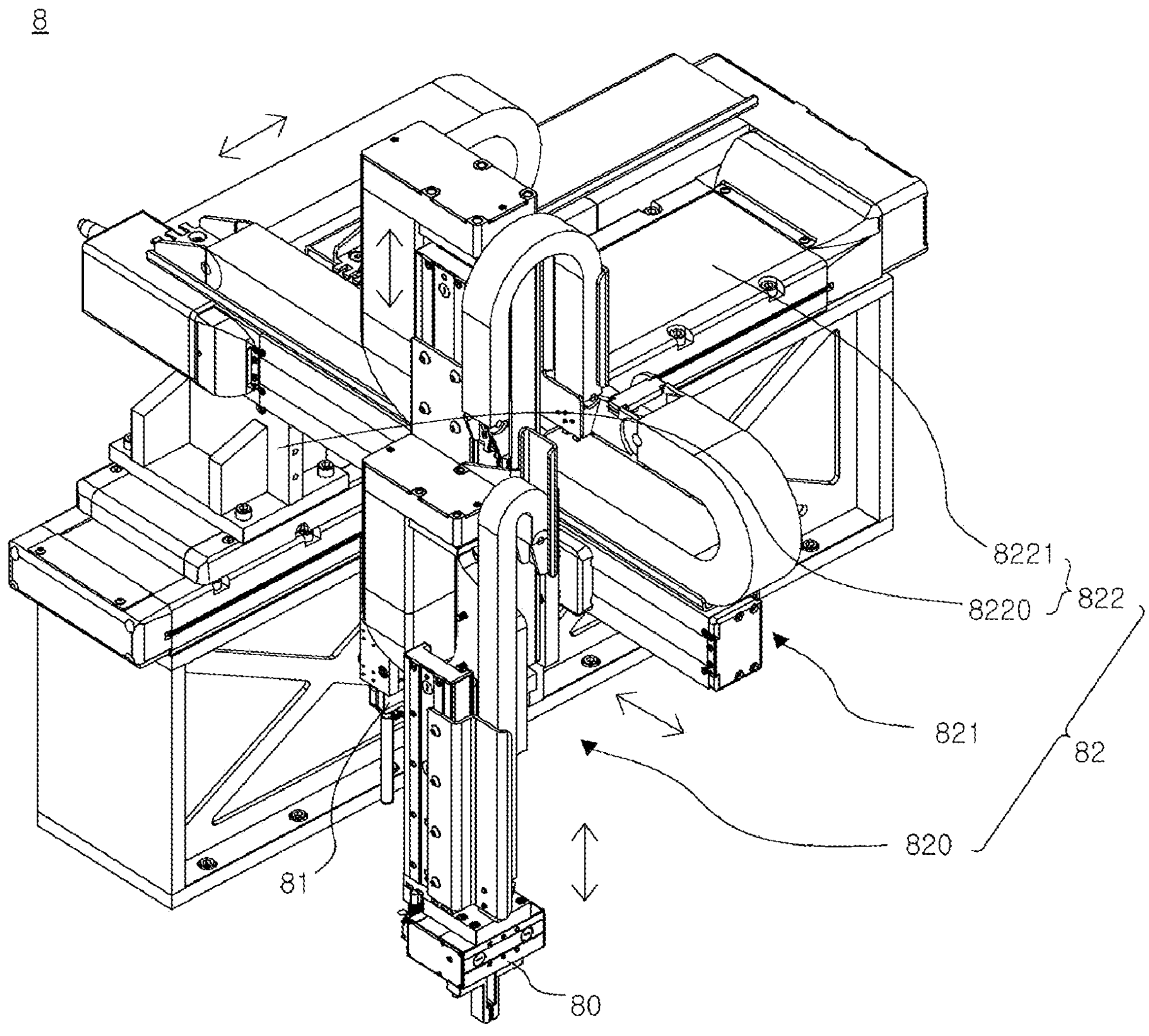
FIG. 11 is a perspective view illustrating a blood sample post-processing unit of FIG. 2.
Figure 12:
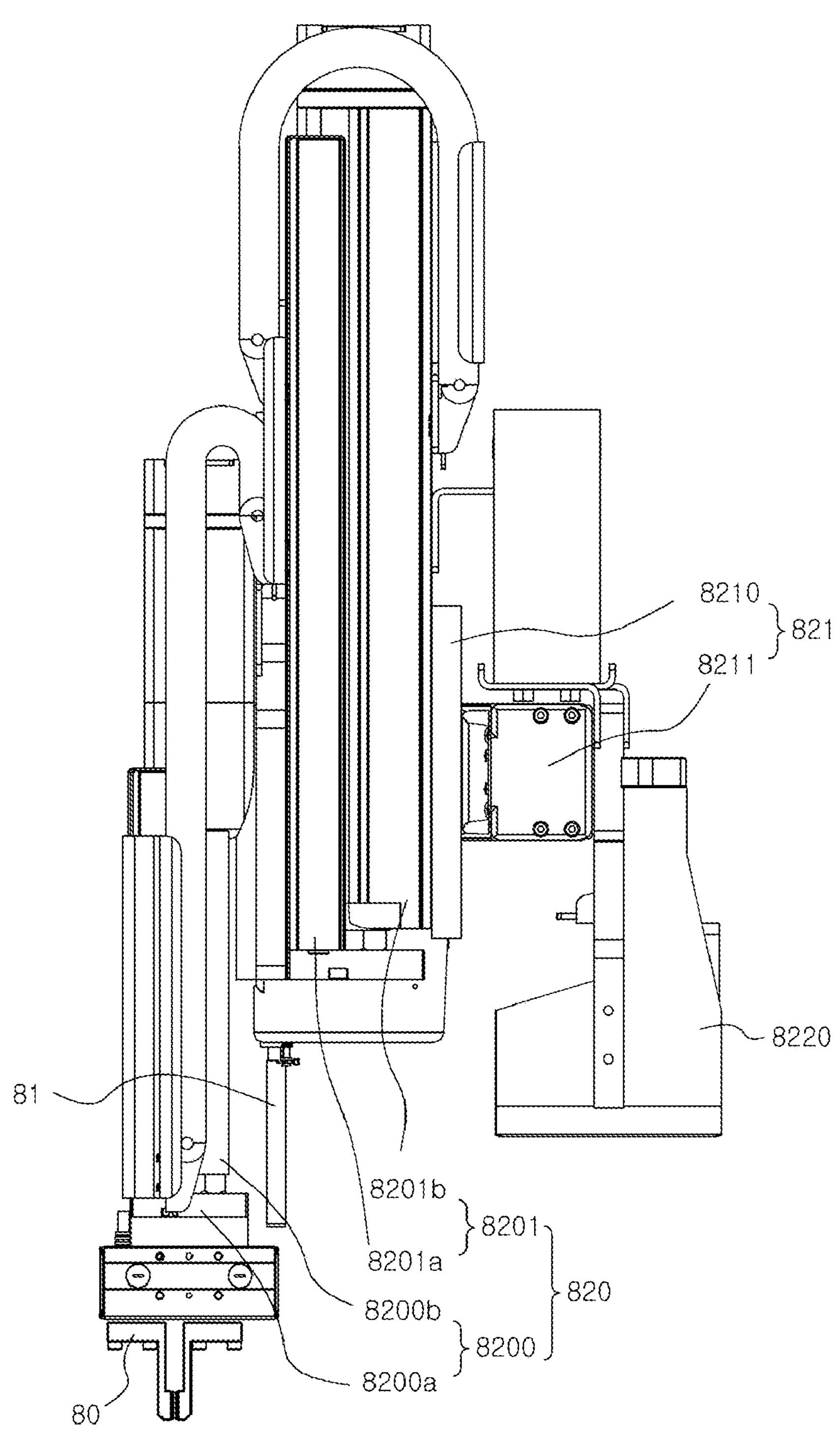
FIG. 12 is an enlarged side view of a post-processing up-and-down adjusting unit of FIG. 11.
Figure 13A:
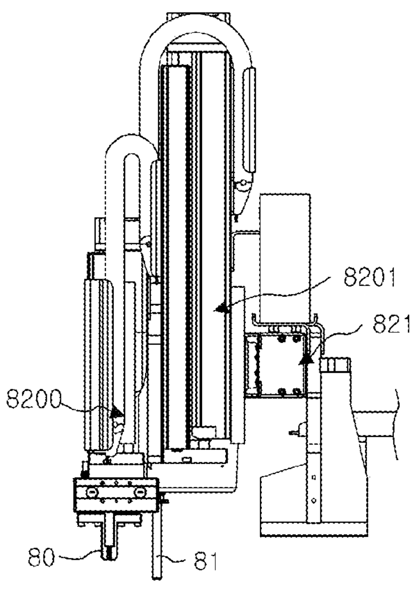
FIGS. 13(*a*) to (*c*) are exemplary operation diagrams illustrating the operation of the post-processing up-and-down adjusting unit of the multi-channel blood viscosity measuring device, according to an embodiment of the present invention.
Figure 13B:
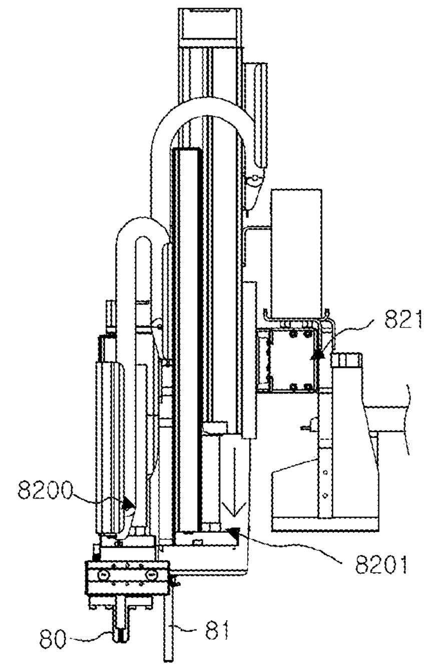
Figure 13C:
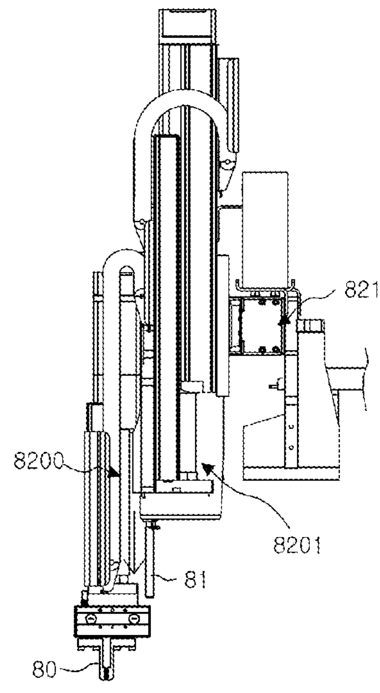

FIG. 1 is a perspective view illustrating a multi-channel blood viscosity measuring device according to an embodiment of the present invention, FIG. 2 is a perspective view illustrating the multi-channel blood viscosity measuring device, a portion of which is removed, according to an embodiment of the present invention, FIG. 3 is a perspective view illustrating a blood sample preprocessing unit of FIG. 2. FIG. 4 is an enlarged perspective view of a preprocessing clamp unit of FIG. 3. FIGS. 5(*a*) and (*b*) are exemplary operation diagrams illustrating a state in which the preprocessing clamp unit of the multi-channel blood viscosity measuring device is operated to scan and shake the blood collection tube, according to an embodiment of the present invention, FIG. 6 is an enlarged side view of a preprocessing up-and-down adjusting unit of FIG. 3. FIG. 7 is a rotational perspective view illustrating a blood sample transfer unit of FIG. 2. FIGS. 8(*a*) and (*b*) are exemplary diagrams illustrating a process of transferring the blood collection tube stably placed on the blood sample transfer unit of the multi-channel blood viscosity measuring device, according to an embodiment of the present invention. FIG. 9 is a rotational perspective view of a blood viscosity measuring unit of FIG. 2. FIGS. 10(*a*) and (*b*) are exemplary operation diagrams illustrating a state in which a blood viscosity measuring kit is mounted and operated in the blood viscosity measuring unit of the multi-channel blood viscosity measuring device, according to an embodiment of the present invention. FIG. 11 is a perspective view illustrating a blood sample post-processing unit of FIG. 2. FIG. 12 is an enlarged side view of a post-processing up-and-down adjusting unit of FIG. 11. FIGS. 13(*a*) to (*c*) are exemplary operation diagrams illustrating the operation of the post-processing up-and-down adjusting unit of the multi-channel blood viscosity measuring device, according to an embodiment of the present invention.

The present invention aims to provide a multi-channel blood viscosity measuring device in which the channel of the blood viscosity measuring unit 7 for measuring the viscosity of the blood sample is formed with multiple channels, and the viscosity of the blood sample accommodated in the blood collection tube is automatically measured without a separate operation by a device operator so that the viscosity of the blood samples is uniformly measured and the time required to measure the viscosity of blood samples in large quantities may be reduced.

Referring to FIGS. 1 and 2, the multi-channel blood viscosity measuring device may include a housing 1, a blood sample mounting unit 2, a blood viscosity measurement cartridge 3, a pipette tip storage unit 4, a blood sample preprocessing unit 5, a blood sample transfer unit 6, a blood viscosity measuring unit 7, a blood sample post-processing unit 8, a waste processing unit 9, a control unit (not illustrated), and a monitor unit 10.

First, components of the multi-channel blood viscosity measuring device may be installed in the housing 1, and the housing 1 may cover the installed components. The housing 1 may include a support housing and a cover housing.

The blood sample mounting unit 2, the blood viscosity measurement cartridge 3, the pipette tip storage unit 4, the blood sample preprocessing unit 5, the blood sample transfer unit 6, the blood viscosity measuring unit 7, the blood sample post-processing unit 8, and the like of the multi-channel blood viscosity measuring device may be installed on the upper surface of the support housing and may be covered by the cover housing, but the present invention is not limited thereto.

In addition, the cover housing is provided with a door so that the user may open the inside of the housing 1 when necessary, such as mounting or removing one or more blood collection tubes B to or from the blood sample mounting unit 2.

The blood sample mounting unit 2 may be formed in a shape of a test tube stand so that the blood collection tube B may be inserted upright. At this time, the plurality of blood collection tubes B may be mounted by including a plurality of blood collection tube mounting holes. The blood sample mounting unit 2 may be formed at one side of the front side on the upper surface of the support housing, but the present invention is not limited thereto.

The blood viscosity measurement cartridge 3 is capable of storing the blood viscosity measuring kit 30 before use. The blood viscosity measurement cartridge 3 is preferably formed to store one or more blood viscosity measuring kits 30. The upper surface of the blood viscosity measurement cartridge 3 may be opened so that the blood sample post-processing unit 8 may easily pick up the blood viscosity measuring kit 30, but the present invention is not limited thereto. The blood viscosity measurement cartridge 3 may be formed at the central side of the front side on the upper surface of the support housing, but the present invention is not limited thereto.

The pipette tip storage unit 4 may store pipette tips before use, and may include a plurality of pipette tip holes into which pipette tips are inserted so as to store one or more pipette tips. The pipette tip storage unit 4 may be formed at the other side of the front side on the upper surface of the support housing, but the present invention is not limited thereto.

The blood sample preprocessing unit 5 may detect one or more blood collection tubes B mounted on the blood sample mounting unit 2, may lift up the blood collection tube B, may scan the blood collection tube B, may shake the blood collection tube B, may stably place the blood collection tube B on the blood sample transfer unit 6, and may remove the blood collection tube cover therefrom.

The blood sample preprocessing unit 5 may be formed at one side of the upper surface of the support housing, but the present invention is not limited thereto.

Referring to FIG. 3, the blood sample preprocessing unit 5 may include a blood collection tube detecting unit 50, a blood sample reader unit 51, a preprocessing clamp unit 52, and a preprocessing position adjusting unit 53.

The blood collection tube detecting unit 50 may be installed at one side of the preprocessing clamp unit 52 and may obtain blood collection tube mounting information, which is information about the locations and number of blood collection tubes B, by detecting one or more blood collection tubes B mounted on the blood sample mounting unit 2.

More specifically, the blood collection tube detecting unit 50 may obtain an image by capturing one or more blood collection tubes B mounted on the blood sample mounting unit 2 through laser scanning or image capturing and may analyze the image to obtain the blood collection tube mounting information, which is information about the locations and number of blood collection tubes B.

In this manner, the blood sample preprocessing unit 5 may automatically lift up or place the blood collection tube B according to the blood collection tube mounting information and may measure the viscosity of the blood samples in all the blood collection tubes B.

The blood sample reader unit 51 may obtain blood sample information by scanning the blood collection tube B. That is, the blood sample reader unit 51 may scan a barcode attached to the blood collection tube B to obtain blood sample information about the blood sample accommodated in the corresponding blood collection tube B.

Accordingly, it is possible to identify the blood sample whose viscosity is being measured, and the measured viscosity measurement result may be automatically stored as a result of the corresponding blood sample information.

In addition, the blood sample reader unit 51 may transmit the obtained blood sample information to the monitor unit 10 so that the user identify the obtained sample information.

The preprocessing clamp unit 52 may hold and rotate the blood collection tube B mounted on the blood sample mounting unit 2. As the position of the preprocessing clamp unit 52 is adjusted by the preprocessing position adjusting unit 53, the preprocessing clamp unit 52 may allow the blood collection tube cover to be removed from the blood collection tube B.

In addition, as the position of the preprocessing clamp unit 52 is adjusted by the preprocessing position adjusting unit 53, the preprocessing clamp unit 52 may insert a blood collection tube cover into the blood collection tube B, to which the blood sample is suctioned and transferred by the blood sample transfer unit 6, and then mount the blood collection tube cover to the blood sample mounting unit 2 again. At this time, the mounting position may be the position where the corresponding blood collection tube B has been mounted.

Referring to FIGS. 4 and 5, the preprocessing clamp unit 52 may include a processing clamp 520, a first rotating unit 521, and a second rotating unit 522.

The preprocessing clamp 520 is formed as a symmetrical pair, and may hold or place the blood collection tube B. In this case, the preprocessing clamp 520 may include a gripping groove 5200 and a hooking portion 5201.

The gripping groove 5200 may be formed in the inner surface of the lower end of the processing clamp 520 so that the upper portion of the blood collection tube B is accommodated. The blood collection tube cover located on the upper portion may be accommodated. Accordingly, the gripping groove 5200 may be preferably formed to correspond to the shape of the cover of the blood collection tube B, but the present invention is not limited thereto.

The hooking portion 5201 may be formed at the lower end of the gripping groove 5200 so that the blood collection tube cover is hung.

Accordingly, the blood collection tube B is stably placed on and fixed to the blood sample transfer unit 6, and the preprocessing clamp unit 52 moves upward in a state where the preprocessing clamp 520 holds the blood collection tube cover of the blood collection tube B, and thus, the blood collection tube cover may be removed from the blood collection tube B.

The first rotating unit 521 may rotate the preprocessing clamp 520 around the z axis. The first rotating unit 521 may be connected to the upper side of the preprocessing clamp 520 and rotated by 360° around the z-axis.

Accordingly, as illustrated in FIG. 5(*a*), the barcode of the blood collection tube B may be easily scanned by rotating the blood collection tube B held by the preprocessing clamp 520 by 360° around the z-axis and scanning the blood sample reader unit 51.

As illustrated in FIG. 5(*b*), the second rotating unit 522 may rotate the preprocessing clamp 520 around the y-axis, but the present invention is not limited thereto. The second rotating unit 522 may rotate the preprocessing clamp 520 around the x-axis.

The second rotating unit 522 may be connected to the upper side of the first rotating unit 521, to rotate the preprocessing clamp 520 around the y-axis.

In the blood sample, red blood cells may sink over time. In this state, when the viscosity of the blood is measured, the measurement accuracy may deteriorate.

Accordingly, the blood collection tube B is shaken through the second rotating unit 522 to mix plasma and blood cells of the blood sample, thereby improving the blood viscosity measurement accuracy.

As described above, the first rotating unit 521 may be connected to the upper side of the preprocessing clamp 520, and the second rotating unit 522 may be connected to the upper side of the first rotating unit 521, but the present invention is not limited thereto. The structure may be variously changed. For example, the second rotating unit 522 may be connected to the upper side of the preprocessing clamp 520 and then the first rotating unit 521 may be connected to the upper side of the second rotating unit 522.

The preprocessing position adjusting unit 53 may be installed in the support housing 1 and connected to the preprocessing clamp unit 52 to adjust the position of the preprocessing clamp unit 52.

To this end, the preprocessing position adjusting unit 53 may include one or more of a preprocessing up-and-down adjusting unit 530, a preprocessing left-and-right adjusting unit 531, and a preprocessing front and rear adjusting unit 532. At this time, all of them may be preferably included to adjust the position of the preprocessing clamp unit 52 by adjusting the up-and-down, left-and-right, and front and rear positions, but the present invention is not limited thereto.

The preprocessing up-and-down adjusting unit 530 may adjust the up-and-down position of the preprocessing clamp unit 52, and may be connected to the preprocessing clamp unit 52 to move the preprocessing clamp unit 52 in the up-and-down direction.

Referring to FIG. 6, the preprocessing up-and-down adjusting unit 530 may include a first up-and-down connecting member 5300 and a first up-and-down adjusting unit 5301.

The first up-and-down connecting member 5300 may be formed in an 'L' shape and connected to the rear side of the preprocessing clamp unit 52, but the shape of the first up-and-down connecting member 5300 is not limited thereto, and the first up-and-down connecting member 5300 may be formed in various shapes.

In addition, the first up-and-down connecting member 5300 may be connected to the first up-and-down adjusting unit 5301 to move in an up-and-down direction, and thus, the preprocessing clamp unit 52 may move in an up-and-down direction. At this time, the first up-and-down adjusting unit 5301 may be preferably connected to the rear side of the lower end, but the present invention is not limited thereto.

The first up-and-down adjusting unit 5301 may be connected to the first up-and-down connecting member 5300 to move the first up-and-down connecting member 5300 up-and-down. To this end, the first up-and-down adjusting unit 5301 may be provided as a cylinder installed vertically on the ground, but the present invention is not limited thereto, and various actuators and devices capable of moving the preprocessing clamp unit 52 up-and-down may be applied.

The preprocessing left-and-right adjusting unit 531 may adjust the position of the preprocessing clamp unit 52 in the left-and-right direction and may be connected to the preprocessing up-and-down adjusting unit 530 to move in the left-and-right direction so that the preprocessing clamp unit 52 may be moved left-and-right.

To this end, the preprocessing left-and-right adjusting unit 531 may include a first left-and-right connecting member 5310 and a first left-and-right adjusting unit 5311.

The first left-and-right connecting member 5310 may be connected to the rear side of the preprocessing up-and-down adjusting unit 530. More specifically, the first left-and-right connecting member 5310 may be connected to the rear side of the first up-and-down adjusting unit 5301. However, the present invention is not limited thereto, and the first up-and-down adjusting unit 5301 and the first left-and-right adjusting unit 5311 may be directly connected without the first left-and-right connecting member 5310.

The first left-and-right adjusting unit 5311 may be connected to the rear side of the first left-and-right connecting member 5310 to move the first left-and-right connecting member 5310 left-and-right so as to move the preprocessing clamp unit 52 left-and-right.

The first left-and-right adjusting unit 5311 may be provided as a linear actuator installed to have a length in the left-and-right direction, but the present invention is not limited thereto, and various types of actuators, rails, and the like may be applied.

The preprocessing front and rear adjusting unit 532 may adjust the position of the preprocessing clamp unit 52 in the front and rear direction, and may be connected to the preprocessing left-and-right adjusting unit 531 and move in the front and rear direction so that the preprocessing clamp unit 52 may be moved front and rear.

To this end, the preprocessing front and rear adjusting unit 532 may include a first front and rear connecting member 5320 and a first front and rear adjusting unit 5321.

The first front and rear connecting member 5320 may be connected to one side of the preprocessing left-and-right adjusting unit 531. More specifically, the first front and rear connecting member 5320 may be connected to one side of the first left-and-right adjusting unit 5311. However, the present invention is not limited thereto, and the first left-and-right adjusting unit 5311 and the first front and rear adjusting unit 5321 may be connected in various forms without the first front and rear connecting member 5320. For example, the first left-and-right adjusting unit 5311 and the first front and rear adjusting unit 5321 may be directly connected to each other.

The first front and rear adjusting unit 5321 may be installed in the support housing and connected to the lower side of the first front and rear connecting member 5320 to move the first front and rear connecting member 5320 front and rear so that the preprocessing clamp unit 52 may be moved front and rear.

The first front and rear adjusting unit 5321 may be provided as a linear actuator installed to have a length in the front and rear direction, but the present invention is not limited thereto, and various types of actuators, rails, and the like may be applied.

As described above, the preprocessing up-and-down adjusting unit 530, the preprocessing left-and-right adjusting unit 531, and the preprocessing front and rear adjusting unit 532 may be connected to the preprocessing clamp unit 52 so as to adjust the positions in the up-and-down, left-and-right, and front and rear directions, but the present invention is not limited thereto, and the connection order may be variously changed.

The operation of the blood sample preprocessing unit 5 will be sequentially described in more detail.

First, the blood collection tube detecting unit 50 detects the blood collection tube B installed in the blood sample mounting unit 2 to obtain blood collection tube mounting information. The preprocessing position adjusting unit 53 may adjust the position of the preprocessing clamp unit 52 according to the obtained blood collection tube mounting information, and the preprocessing clamp unit 52 may hold the blood collection tube B.

Next, the preprocessing clamp unit 52 is moved by the preprocessing position adjusting unit 53, and the blood sample reader 51 scans the blood collection tube B. At this time, the first rotating unit 521 of the preprocessing clamp unit 52 may rotate and scan the blood collection tube B.

Thereafter, the second rotating unit 522 of the preprocessing clamp unit 52 may operate to shake the blood collection tube B.

Thereafter, when the preprocessing clamp unit 52 is moved by the preprocessing position adjusting unit 53 so that the blood collection tube B is stably placed on the blood sample transfer unit 6 and the blood collection tube B is fixed to the blood sample transfer unit 6, the preprocessing clamp unit 52 may be raised by the preprocessing position adjusting unit 53 and the blood collection tube cover may be removed from the blood collection tube B.

Thereafter, when the blood collection tube B into which the blood sample is suctioned is transferred through the blood sample transfer unit 6, the preprocessing clamp unit 52 may be lowered by the preprocessing position adjusting unit 53 so that the blood collection tube cover may be inserted into the blood collection tube B. When the blood collection tube cover is inserted, the fixation of the blood collection tube B by a transfer clamp unit 60 may be released.

Thereafter, the preprocessing clamp unit 52 is moved by the preprocessing position adjusting unit 53 so that the blood collection tube B may be mounted again at the original position of the blood sample mounting unit 2.

The blood sample preprocessing unit 5 may measure the viscosity of the plurality of blood samples by repeating the above process.

Referring to FIGS. 7 and 8, the blood sample transfer unit 6 may move the blood collection tube B stably placed by the blood sample preprocessing unit 5 in the left-and-right direction and may include a transfer unit 60 and a transfer unit 61.

The blood collection tube B may be stably placed by the blood sample preprocessing unit 5, and the transfer clamp unit 60 may fix the stably placed blood collection tube B. To this end, the transfer clamp unit 60 may include a seating member 600 and a transfer clamp 601.

The seating member 600 may be provided with a tube seating groove in which the blood collection tube B is seated.

The transfer clamp 601 may be installed at one side of the seating member 600 to fix the blood collection tube B seated in the tube seating groove. In addition, the transfer clamp 601 may be opened when the transfer clamp unit 60 is moved from the other side to one side, and thus, the fixing of the blood collection tube B may be released.

The transfer unit 61 may be connected to the transfer clamp unit 60, and the transfer clamp unit 60 may be moved in the left-and-right direction (both directions) by the transfer unit 61.

The transfer unit 61 may be connected to the transfer clamp unit 60 to transfer the seated blood collection tube B. Specifically, when the blood collection tube B is seated on the transfer clamp unit 60, and the blood collection tube cover is removed, the transfer unit 61 may transfer the transfer clamp unit 60 from one side to the other, and when the blood sample of the blood collection tube B is suctioned, the transfer unit 61 may transfer the transfer clamp unit 60 from the other side to one side. The above process may be automatically repeated.

The transfer unit 61 may be provided as a linear actuator installed to have a length in the left-and-right direction, but the present invention is not limited thereto, and various types of actuators, rails, and the like may be applied.

The blood sample transfer unit 6 may be formed between the blood sample preprocessing unit 5 and the blood sample post-processing unit 8 on the upper surface of the support housing, but the present invention is not limited thereto.

Referring to FIG. 9, the blood viscosity measuring unit 7 may measure the viscosity of the blood sample by using the blood viscosity measuring kit 30 and may include one or more channels 70. The blood viscosity measuring unit 7 may preferably include a plurality of channels 70 so that the viscosity of the plurality of blood samples may be measured at the same time. Although FIG. 9 illustrates that the blood viscosity measuring unit 7 includes eight channels, the present invention is not limited thereto.

The blood viscosity measuring kit 30 may be mounted on the channel 70 to measure the viscosity of the injected blood sample.

The channel 70 may include a kit mounting member 700, a kit guide member 701, a viscosity measuring unit 702, and a kit inserting unit 703.

The blood viscosity measuring kit 30 may be mounted on the kit mounting member 700, and the kit mounting member 700 may be moved along the kit guide member 701 by the kit inserting unit 703 and inserted into the viscosity measuring unit 702. When the kit mounting member 700 is inserted into the viscosity measuring unit 702 in a state where the blood viscosity measuring kit 30 is mounted, the blood sample may be injected into the blood viscosity measuring kit 30 from the blood sample post-processing unit 8.

In addition, the kit mounting member 700 may include a kit mounting groove on which the blood viscosity measuring kit 30 may be mounted, and the kit inserting unit 703 may be connected to the other side.

The kit guide member 701 may include a movable guide on which the kit mounting member 700 is installed. In addition, the viscosity measuring unit 702 may be installed to be connected to one side of the kit mounting member 700, so that the kit mounting member 700 moved along the guide may be inserted into the viscosity measuring unit 702.

The viscosity measuring unit 702 may be installed to be connected to one side of the kit guide member 701, so that the kit mounting member 700 mounted with the blood viscosity measuring kit 30 is inserted inside and the viscosity of the blood sample injected into the blood viscosity measuring kit 30 may be measured.

In addition, the viscosity measuring unit 702 may include a viscosity measuring housing and an optical sensor (not illustrated).

The viscosity measuring housing may be formed in a box shape, and the other side of the viscosity measuring housing may be opened so that the blood viscosity measuring kit 30 may be inserted or withdrawn, but the present invention is not limited thereto.

In addition, a portion of the other side of the upper surface of the viscosity measuring housing may be formed to be opened so that the blood sample may be injected in a state where the blood viscosity measuring kit 30 is inserted therein, but the present invention is not limited thereto.

The optical sensor may measure the change in the height of the blood sample injected into the blood viscosity measuring kit 30 over time, and may measure the viscosity of the blood sample. The viscosity measurement result may be transmitted to the monitor unit 10.

Referring to FIG. 10, the kit inserting unit 703 may be connected to the other side of the kit mounting member 700. When the blood viscosity measuring kit 30 is inserted into the kit mounting member 700, the kit mounting member 700 may be inserted into the viscosity measuring unit 702.

In addition, when the viscosity measurement of the viscosity measuring unit 702 is completed, the kit inserting unit 703 may withdraw the kit mounting member 700 from the viscosity measuring unit 702 so that the blood viscosity measuring kit 30 may be processed.

To this end, the kit inserting unit 703 is provided as a cylinder and installed horizontally on the kit mounting member. The kit inserting unit 703 may insert or withdraw the kit mounting member 700 into or from the viscosity measuring unit 702 by the inserting or withdrawing operation, but the present invention is not limited thereto, and various actuators or devices (rails, belts, etc.) capable of moving the viscosity measuring unit 702 may be applied.

The blood sample post-processing unit 8 may mount the blood viscosity measuring kit 30 on the blood viscosity measuring unit 7, may mount the pipette tip to suction the blood sample from the blood collection tube B transferred by the blood sample transfer unit 6, and may inject the blood sample into the blood viscosity measuring kit 30. In addition, the pipette tip and the blood viscosity measuring kit 30 used herein may be discarded in the waste processing unit 9.

Referring to FIG. 11, the blood sample post-processing unit 8 may include a kit clamp unit 80, a pipette unit 81, and a post-processing position adjusting unit 82.

The position of the kit clamp unit 80 may be adjusted by the post-processing position adjusting unit 82, so that the blood viscosity measuring kit 30 may be held or placed thereon.

The pipette unit 81 may be mounted with the pipette tip to suction the blood sample of the blood collection tube B and inject the blood sample into the blood viscosity measuring kit 30. The position may be adjusted by the post-processing position adjusting unit 82 so that the pipette tip in the pipette tip storage unit 4 may be mounted, and the blood sample may be suctioned and injected. In addition, the used pipette tip may be discarded in the waste processing unit 9.

The post-processing position adjusting unit 82 may be installed in the support housing and connected to the kit clamp unit 80 and the pipette unit 81 to adjust the positions of the kit clamp unit 80 and the pipette unit 81.

To this end, the post-processing position adjusting unit 82 may include one or more of a post-processing up-and-down adjusting unit 820, a post-processing left-and-right adjusting unit 821, and a post-processing front and rear adjusting unit 822. At this time, all of them may be preferably included to adjust the positions of the kit clamp unit 80 and the pipette unit 81 by adjusting the up-and-down, left-and-right, and front and rear positions, but the present invention is not limited thereto.

The post-processing up-and-down adjusting unit 820 may adjust the positions of the kit clamp unit 80 and the pipette unit 81 in the up-and-down direction.

At this time, a collision may occur when the position of the kit clamp unit 80 and the pipette unit 81, which have a difference in length, are equally adjusted in the vertical direction. Thus, it is preferable that the positions of the kit clamp unit 80 and the pipette unit 81 in the up-and-down direction is separately adjusted.

Accordingly, the post-processing up-and-down adjusting unit 820 may include a kit up-and-down adjusting unit 8200 and an integrated up-and-down adjusting unit 8201.

The kit up-and-down adjusting unit 8200 may be connected to the kit clamp unit 80 to move the kit clamp unit 80 in the up-and-down direction.

Referring to FIGS. 12 and 13, the kit up-and-down adjusting unit 8200 may include a kit up-and-down connecting member 8200*a* and a kit up-and-down adjusting unit 8200*b*.

The kit up-and-down connecting member 8200*a* may be formed in an 'L' shape and connected to the upper side of the kit clamp unit 80, but the shape of the kit up-and-down connecting member 8200*a* is not limited thereto, and the kit up-and-down connecting member 8200*a* may be formed in various shapes.

In addition, the kit up-and-down adjusting unit 8200*b* may be connected to the kit up-and-down connecting member 8200*a* to move up-and-down, and thus, the kit clamp unit 80 may move in an up-and-down direction. At this time, the kit up-and-down adjusting unit 8200*b* may be preferably connected to the rear side of the lower end, but the present invention is not limited thereto.

The kit up-and-down adjusting unit 8200*b* may be connected to the kit up-and-down connecting member 8200*a* to move the kit up-and-down connecting member 8200*a* up-and-down.

To this end, the kit up-and-down adjusting unit 8200*b* may be provided as a cylinder installed vertically on the ground, but the present invention is not limited thereto, and various actuators and devices capable of moving the kit clamp unit 80 up-and-down may be applied.

The integrated up-and-down adjusting unit 8201 may include an integrated up-and-down connecting member 8201*a* and an integrated up-and-down adjusting unit 8201*b*.

The integrated up-and-down connecting member 8201*a* may be formed in an 'L' shape and connected to the rear side of the kit up-and-down adjusting unit 8200 and the pipette unit 81, but the shape of the integrated up-and-down connecting member 8201*a* is not limited thereto, and the integrated up-and-down connecting member 8201*a* may be formed in various shapes.

In addition, the integrated up-and-down connecting member 8201*a* may be connected to the integrated up-and-down adjusting unit 8201*b* and moved in an up-and-down direction so that the kit clamp unit 80 and the pipette unit 81 may be moved in the up-and-down direction together. At this time, the integrated up-and-down adjusting unit 8201*b* may be preferably connected to the rear side of the lower end, but the present invention is not limited thereto.

The integrated up-and-down adjusting unit 8201*b* may be connected to the integrated up-and-down connecting member 8201*a* to move the integrated up-and-down connecting member 8201*a* up-and-down.

To this end, the integrated up-and-down adjusting unit 8201*b* may be provided as a cylinder installed vertically on the ground, but the present invention is not limited thereto, and various actuators and devices capable of moving the kit clamp unit 80 and the pipette unit 81 up-and-down may be applied.

In addition, the post-processing left-and-right adjusting unit 821 may be connected to the rear side of the integrated up-and-down adjusting unit 8201*b*, but the present invention is not limited thereto.

The post-processing left-and-right adjusting unit 821 may adjust the positions of the kit clamp unit 80 and the pipette unit 81 in the left-and-right direction, and may be connected to the post-processing up-and-down adjusting unit 820 to move the post-processing up-and-down adjusting unit 820 in the left-and-right direction so that the kit clamp unit 80 and the pipette unit 81 may be moved left-and-right.

To this end, the post-processing left-and-right adjusting unit 821 may include a second left-and-right connecting member 8210 and a second left-and-right adjusting unit 8211.

The second left-and-right connecting member 8210 may be connected to the rear side of the post-processing up-and-down adjusting unit 820. More specifically, the second left-and-right connecting member 8210 may be connected to the rear side of the integrated up-and-down adjusting unit 8201*b*. However, the present invention is not limited thereto, and the integrated up-and-down adjusting unit 8201*b* and the second left-and-right adjusting unit 8211 may be directly connected at various positions without the second left-and-right connecting member 8210. For example, the integrated up-and-down adjusting unit 8201*b* and the second left-and-right adjusting unit 8211 may be directly connected to each other.

The second left-and-right adjusting unit 8211 may be connected to the rear side of the second left-and-right connecting member 8210 to move the second left-and-right connecting member 8210 left-and-right, so that the kit clamp unit 80 and the pipette unit 81 may move left-and-right.

The second left-and-right adjusting unit 8211 may be provided as a linear actuator like the first left-and-right adjusting unit 5311, but the present invention is not limited thereto.

The post-processing front and rear adjusting unit 822 may adjust the positions of the kit clamp unit 80 and the pipette unit 81 in the front and rear direction, and may be connected to the post-processing left-and-right adjusting unit 821 to move the post-processing left-and-right adjusting unit 820 in the front and rear direction so that the kit clamp unit 80 and the pipette unit 81 may be moved front and rear.

To this end, the post-processing front and rear adjusting unit 822 may include a second front and rear connecting member 8220 and a second front and rear adjusting unit 8221. The post-processing front and rear adjusting unit 822 may be substantially the same device as the preprocessing front and rear adjusting unit 532, except that the installed position and direction and the connected components are different.

The second front and rear connecting member 8220 may be connected to one side of the post-processing left-and-right adjusting unit 821.

The second front and rear adjusting unit 8221 may be installed in the support housing and connected to the lower side of the second front and rear connecting member 8220 to move the second front and rear connecting member 8220 front and rear, so that the kit clamp unit 80 and the pipette unit 81 may be moved front and rear.

In this case, the second front and rear adjusting unit 8221 may be provided as a linear actuator like the first front and rear adjusting unit 5321, but the present invention is not limited thereto.

In the post-processing position adjusting unit 82, the post-processing up-and-down adjusting unit 820, the post-processing left-and-right adjusting unit 821, and the post-processing front and rear adjusting unit 822 may be connected to the kit clamp unit 80 and the pipette unit 81 to adjust the positions in the up-and-down, left-and-right, and front and rear directions, but the connection order may be variously changed.

The operation of the blood sample post-processing unit 8 will be sequentially described in more detail.

First, the positions of the kit clamp unit 80 and the pipette unit 81 may be adjusted by the post-processing position adjusting unit 82, and the kit clamp unit 80 may be moved downward by the kit up-and-down adjusting unit 8200 to hold the blood viscosity measuring kit 30. The blood viscosity measuring kit 30 may be held and then moved by the post-processing position adjusting unit 82 so that the blood viscosity measuring kit 30 may be mounted on the blood viscosity measuring unit 7.

Thereafter, the kit clamp unit 80 and the pipette unit 81 may be moved by the post-processing position adjusting unit 82 so that the pipette tip may be mounted on the pipette unit 81.

Thereafter, the kit clamp unit 80 and the pipette unit 81 may be moved by the post-processing position adjusting unit 82, and the pipette unit 81 suctions the blood sample of the blood collection tube B transferred to the other side by the blood sample transfer unit 6, and the blood sample may be injected into the blood viscosity measuring kit 30 moved by the post-processing position adjusting unit 82 and mounted on the blood viscosity measuring unit 7.

Thereafter, the used pipette tip moved by the post-processing position adjusting unit 82 may be discarded in the waste processing unit 9.

The blood sample post-processing unit 8 may measure the viscosity of the plurality of blood samples by repeating the above process.

Additionally, the blood sample post-processing unit 8 may process the blood viscosity measuring kit 30, which has been measured by the blood viscosity measuring unit 7, through the waste processing unit 9 while repeating the above process.

The blood sample preprocessing unit 5, the blood sample transfer unit 6, and the blood sample post-processing unit 8 repeatedly perform the respective operations to automatically and uniformly perform viscosity measurement for the plurality of blood samples.

The waste processing unit 9 may be formed in the support housing to accommodate the used blood viscosity measuring kit 30 and the used pipette tip and process the used blood viscosity measuring kit 30 and the used pipette tip later.

The control unit (not illustrated) may control the operation of the multi-channel blood viscosity measuring device, such as the blood sample preprocessing unit 5, the blood sample transfer unit 6, and the blood viscosity measuring unit 7.

For example, the control unit may operate the blood sample preprocessing unit 5 according to blood collection tube mounting information received from the blood collection tube detecting unit 50.

The number of repetitions of each component of the multi-channel blood viscosity measuring device may be determined according to number information of the blood collection tube mounting information, and the operation may be controlled accordingly.

In addition, the control unit may receive information from each component and transmit the information to the monitor unit 10, and may receive control setting information from the monitor unit 10 and control the operation of each component accordingly.

The monitor unit 10 may receive, from the control unit, the blood collection tube mounting information detected by the blood collection tube detecting unit 50, the blood sample information obtained by scanning the blood collection tube B from the blood sample reader unit 51, and the viscosity measurement result measured from the channel 70 of the blood viscosity measuring unit 7 and output the received information to allow the user to monitor the information.

In addition, the monitor unit 10 may receive and provide a variety of information of the multi-channel blood viscosity measuring device, such as operation information and state information of each component.

In addition, the monitor unit 10 may receive the control setting information from the user and control each configuration through the control unit.

The blood viscosity measuring kit 30 used in the multi-channel blood viscosity measuring device according to the embodiment of the present invention will be described in detail below with reference to FIGS. 14 to 20.

Figure 14:
FIG. 14 is a perspective view illustrating the blood viscosity measuring kit of the multi-channel blood viscosity measuring device, according to an embodiment of the present invention.
Figure 14:
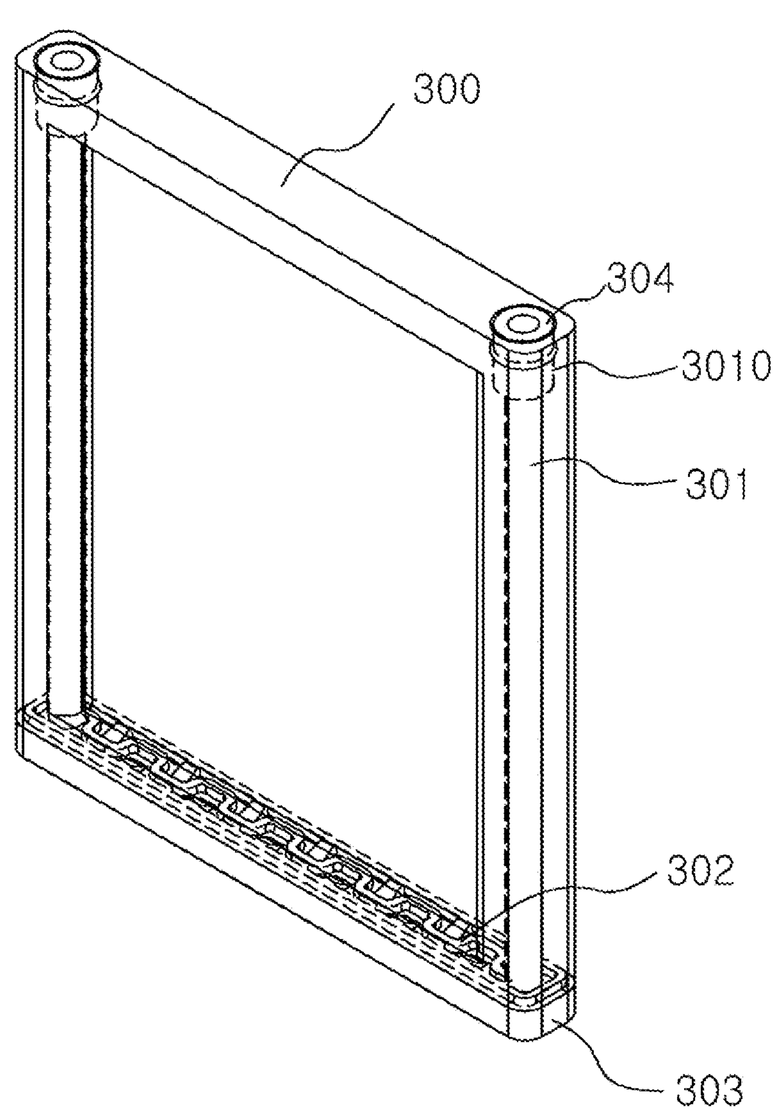
Figure 15:
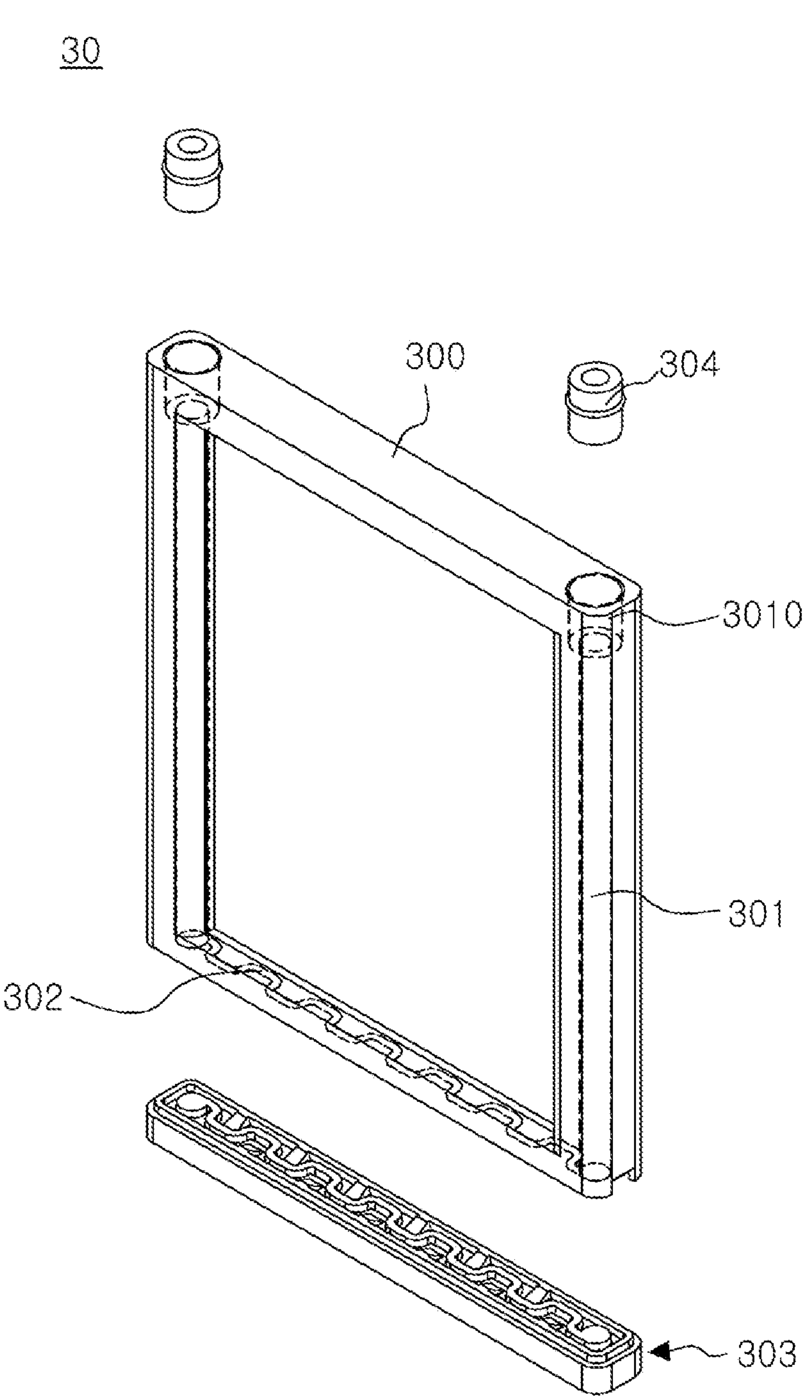
FIG. 15 is an exploded perspective view illustrating the blood viscosity measuring kit of FIG. 14.
Figure 16A:
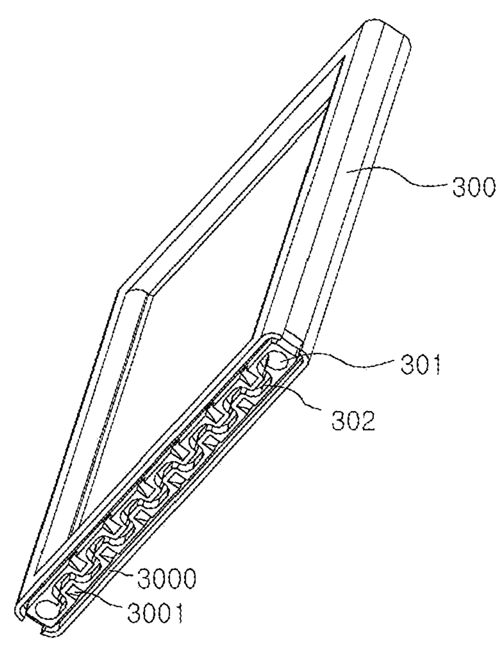
FIGS. 16(*a*) and 16(*b*) are respectively a bottom perspective view and a bottom view illustrating micro-channels formed in a kit body of FIG. 15.
Figure 16B:
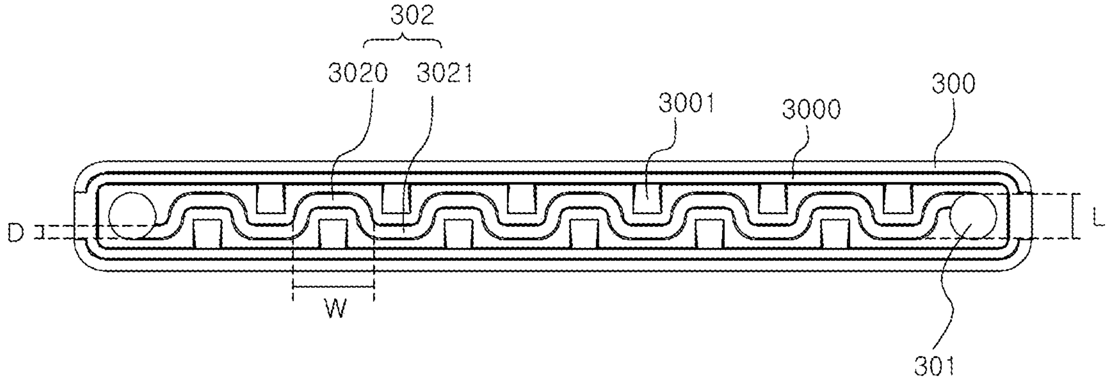
Figure 17:
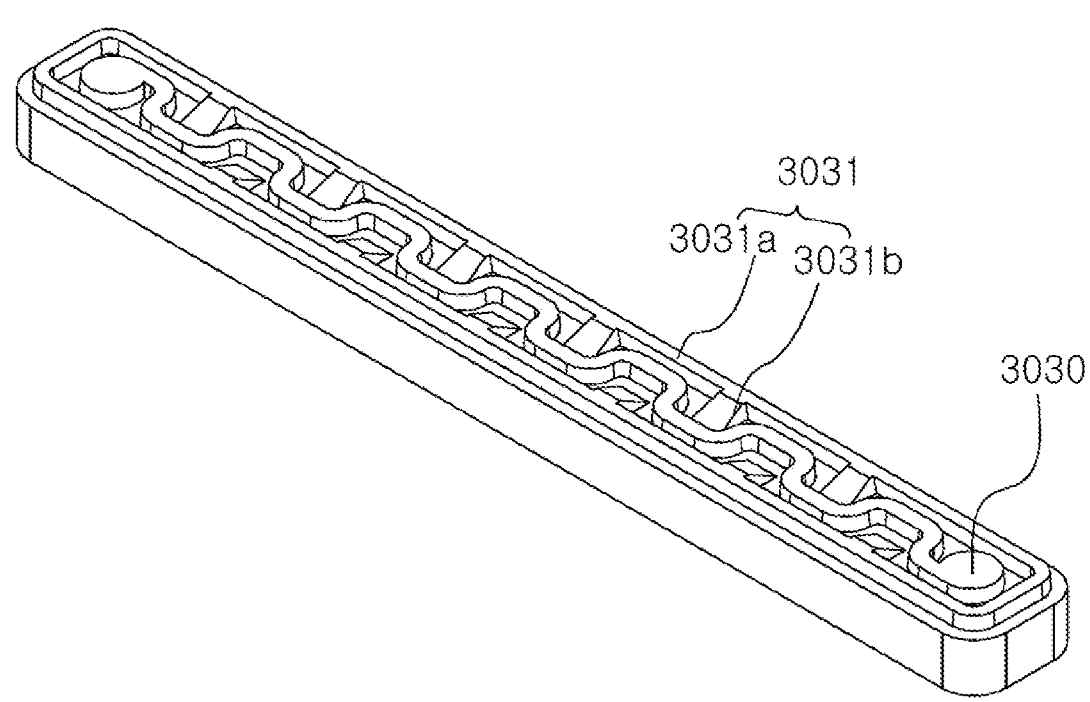
FIG. 17 is a perspective view illustrating a micro-channel cover of FIG. 15.
Figure 18:
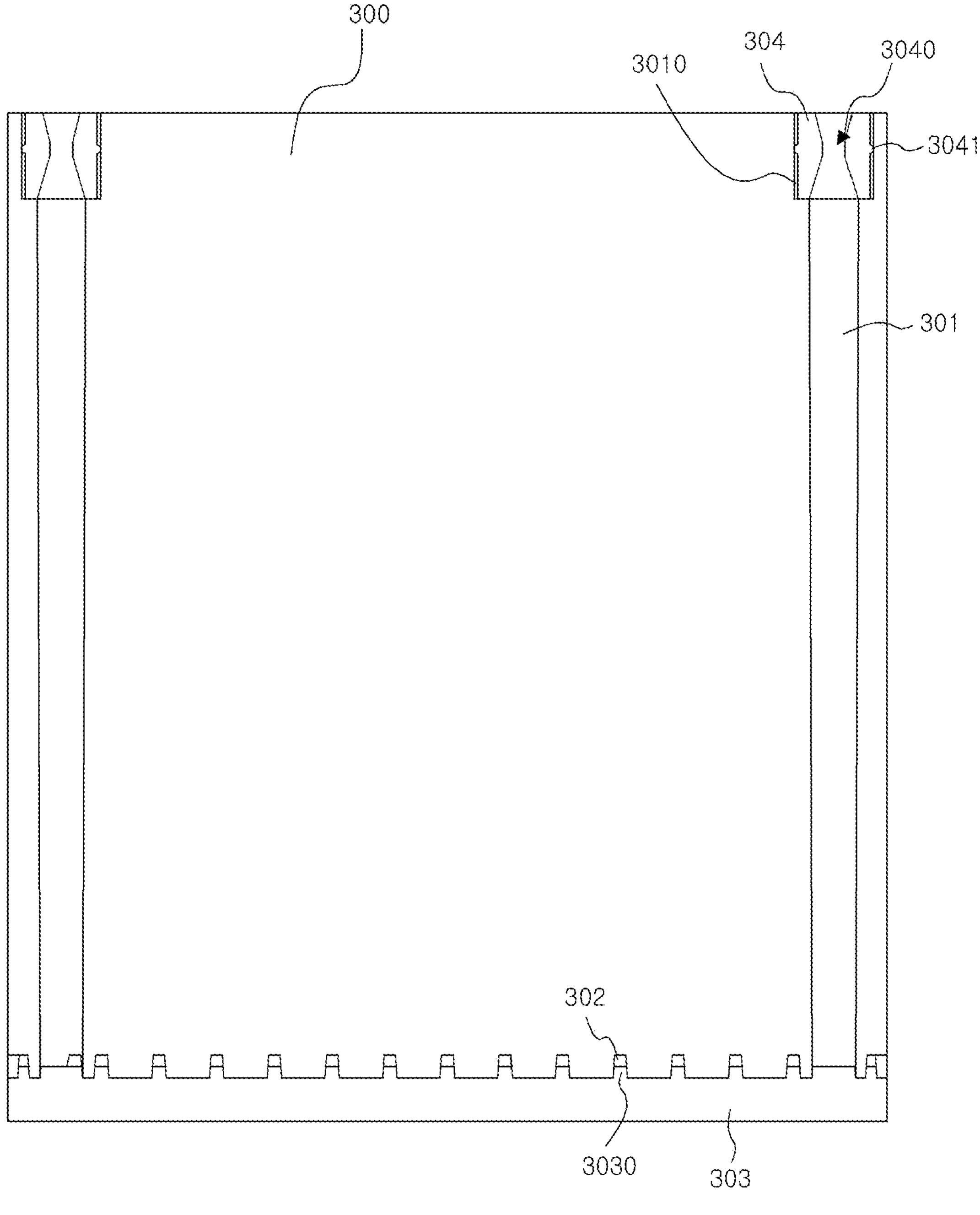
FIG. 18 is a front sectional view illustrating the blood viscosity measuring kit of FIG. 14.
Figures 19A, 19B:
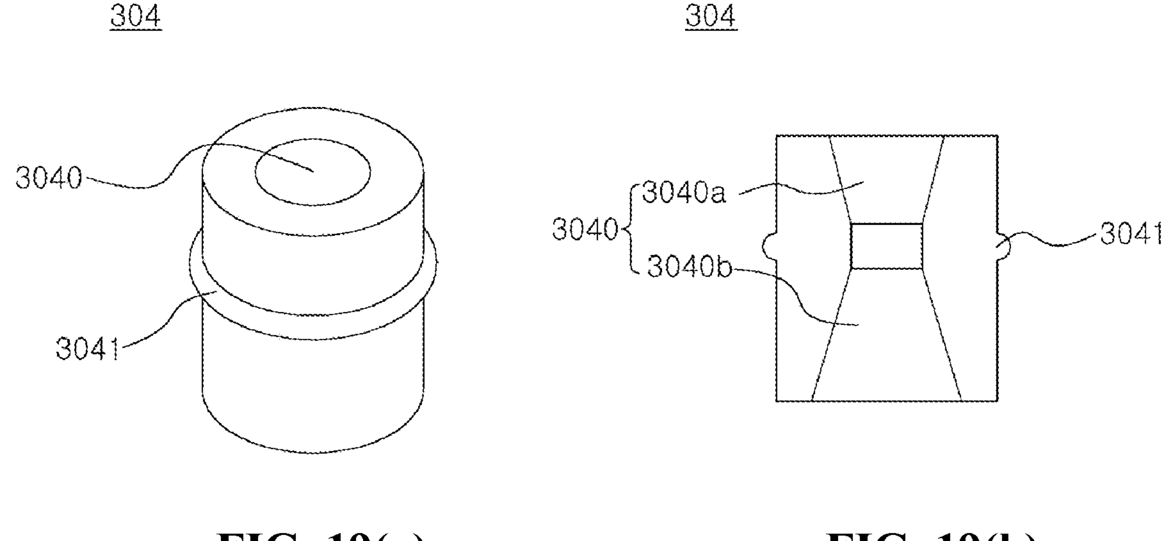
FIGS. 19(*a*) and 19(*b*) are, respectively, a perspective view and a cross-sectional view of an injection cover of FIG. 15.
Figure 20A:
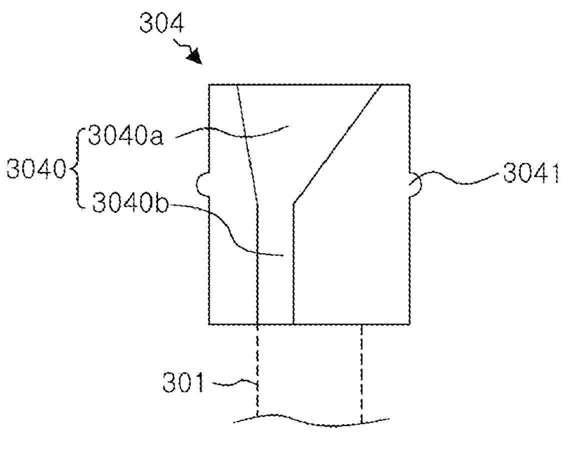
FIGS. 20(*a*) to (*d*) are exemplary diagrams illustrating blood injection holes of the injection cover of FIG. 19, which are formed in different shapes.
Figure 20B:
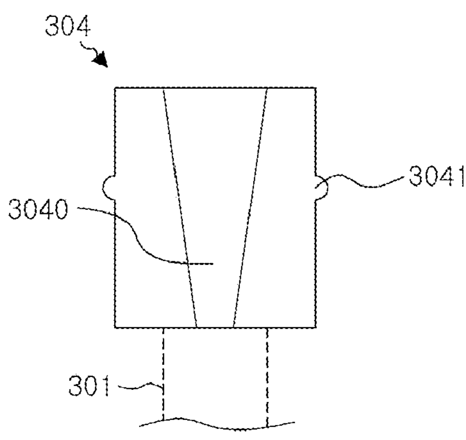
Figure 20C:
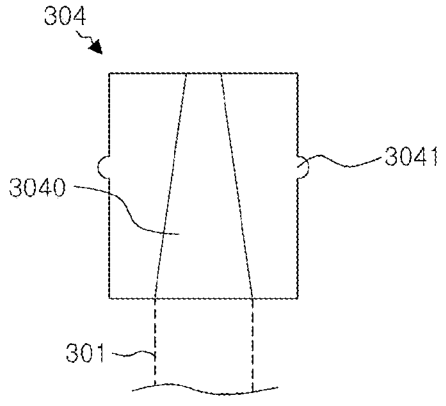
Figure 20D:
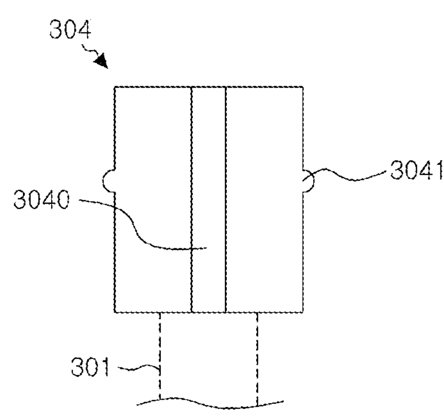

FIG. 14 is a perspective view illustrating the blood viscosity measuring kit of the multi-channel blood viscosity measuring device, according to an embodiment of the present invention, FIG. 15 is an exploded perspective view illustrating the blood viscosity measuring kit of FIG. 14, FIGS. 16(*a*) and (*b*) are, respectively, a bottom perspective view and a bottom view illustrating micro-channels formed in a kit body of FIG. 15, FIG. 17 is a perspective view illustrating a micro-channel cover of FIG. 15, FIG. 18 is a front sectional view illustrating the blood viscosity measuring kit of FIG. 14, FIGS. 19(*a*) and (*b*) are, respectively, a perspective view and a cross-sectional view of an injection cover of FIG. 15, and FIGS. 20(*a*) to (*d*) are exemplary diagrams illustrating blood injection holes of the injection cover of FIG. 19, which are formed in different shapes.

Referring to FIGS. 14 and 15, the blood viscosity measuring kit 30, according to an embodiment of the present invention, may include a kit body 300, blood tubes 301 on both sides, micro-channels 302, a micro-channel cover 303, and an injection cover 304.

The kit body 300 may be formed of a transparent material, and the blood tubes 301 and the micro-channels 302 may be formed to allow blood to flow thereinto. In this way, the inside is formed of a transparent structure so that the situation in which blood is moved in the blood tubes 301 and the micro-channels 302 may be checked in real-time.

Accordingly, an error may be recognized during blood viscosity measurement.

In addition, the kit body 300 is formed within about 60 mm×70 mm (width×height) and is preferably formed in a small size. This may reduce the amount of blood required for blood viscosity measurement. It is necessary to preheat the kit to 36.5° C. so as to make an environment similar to that of the human body when injecting blood. The preheating may be done quickly.

In addition, the kit body 300 may include a first coupling groove 3000 and a second coupling groove 3001 so that the micro-channel cover 303 may be coupled and fixed.

The first coupling groove 3000 may be formed along the outer circumferential surface of the bottom surface of the kit body 300, and a first coupling protrusion 3031*a* may be inserted into the first coupling groove 3000.

The second coupling groove 3001 may be formed adjacent to the first coupling groove 3000. A plurality of second coupling grooves 3001 may be formed in a zigzag manner toward the front and rear along the longitudinal direction, and second coupling protrusions 3031*b* may be inserted into the plurality of second coupling grooves 3001. That is, the second coupling groove 3001 may be formed to be positioned between a first bent portion 3020 and a first bent portion 3020 and between a second bent portion 3021 and a second bent portion 3021.

In addition, the upper surface of the second coupling groove 3001 may be inclined downward from the outside to the inside.

The blood tubes 301 may be formed symmetrically on both sides of the kit body 300, and the upper sides thereof may be opened so that blood may be injected thereinto. Here, the blood tubes 301 may be formed to have a length perpendicular to the upper surface of the kit body 300 when viewed from the front, but the present invention is not limited thereto, and the blood tubes 301 may be inclined downward from both sides of the upper end of the kit body 300 towards the center.

In addition, the lower surfaces of the blood tubes 301 may be opened, so that the opened lower sides thereof may be sealed by the micro-channel cover 303. Accordingly, the blood injected into the blood tubes 301 may flow into the micro-channels 302 without leaking to the outside.

In addition, the blood tubes 301 may include a cover insertion groove 3010, into which the injection cover 304 may be inserted, at the upper end.

The cover insertion groove 3010 may be formed to have a diameter greater than that of the blood tubes 301 at the upper end of the blood tubes 301. The cover insertion groove 3010 may be formed to correspond to the size of the injection cover 304, so that the injection cover 304 may be inserted thereinto.

In addition, the lower ends of the blood tubes 301 may be connected by the micro-channel 302.

Accordingly, when blood is injected into one blood tube 301, the blood may be supplied to the other blood tube 301 through the micro-channels 302.

The micro-channel 302 may be connected to the lower sides of the blood tubes 301 to connect the two blood tubes 301 to each other.

The micro-channel 302 may connect the blood tubes 301 to each other and may have a length in the left-and-right directions, so that blood may flow, but may be formed to be bent.

When the micro-channel 302 is formed in a straight line, there is a limitation in that suitable flow resistance cannot be generated. Due to this limitation, blood fluctuation may occur when the heights of blood in the blood tubes 301 become equal to each other. Therefore, this is done for forming the micro-channel 302 bent to freely form a flow resistance to a desired magnitude and prevent fluctuation from occurring.

Specifically, the micro-channel 302 may include a first bent portion 3020 bent forward and a second bent portion 3021 bent backward, as illustrated in FIG. 16. The first bent portion 3020 and the second bent portion 3021 may be alternately formed in the left-and-right direction in a wave shape.

At this time, the first bent portion 3020 and the second bent portion 3021 may be preferably formed in a symmetrical shape, and may be formed to be bent in various shapes such as a 'U' shape, a semicircular shape, a 'L' shape, or a 'V' shape.

When the micro-channel 302 is formed as described above, the flow fluctuation may be minimized, and the flow resistance of the micro-channel 302 may be easily adjusted. Therefore, when the heights of blood in the blood tubes 301 become equal to each other, the heights of the blood may be adjusted to a desired flow velocity.

A constant blood viscosity measurement is possible only when a flow velocity is constantly maintained by lowering a flow resistance to increase a flow velocity when the amount of blood whose viscosity is measured is small and by increasing a flow resistance to decrease a flow velocity when the amount of blood is large. Therefore, the control of the flow resistance of the micro-channel 302 may be said to be very important.

Conventionally, in order to adjust the flow velocity, methods of adjusting flow resistance by reducing the size of the channel or making the roughness inside the channel coarser have been used, but these methods have limitations in adjusting the flow resistance to a desired magnitude.

However, by forming the micro-channel 302 in the above-described structure, one or more of the total number of first and second bent portions, the width W of the first and second bent portions, and the distance L of the micro-channel may be adjusted. The flow resistance of the micro-channel 302 may be easily adjusted according to a desired condition.

For example, the flow velocity may be adjusted to be slow or fast by increasing the total number of first bend and the second bent portions to increase the flow resistance, or by reducing the total number of first and second bent portions to decrease the flow resistance.

In addition, the size D of the micro-channel 302 may be at least 0.8 mm or more. This is because blood is a mixture of red blood cells, white blood cells, and platelets in plasma components such as water, and thus, when the micro-channel 302 is formed to less than 0.8 mm, red blood cells, white blood cells, platelets, and the like are gathered only in the center of the micro-channel 302, frictional resistance by cells is ignored, and accurate blood viscosity cannot be measured.

It is preferable that the micro-channel 302 is formed on the bottom surface of the kit body 300 so that the lower surface of the micro-channel 302 is opened. At this time, the opened lower side of the micro-channel 302 may be sealed by the micro-channel cover 303.

This makes it easy to manufacture the bent micro-channel 302 and allows the micro-channel 302 to be opened by removing the micro-channel cover 303 so that it can be easily cleaned and disinfected after use. Alternatively, even at the time of discard, the blood may be easily washed away and discarded so that it can be kept clean.

The micro-channel cover 303 may be mounted on the lower portion of the kit body 300 to seal the opened lower sides of the micro-channel 302 and the blood tubes 301.

As illustrated in FIG. 17, the micro-channel cover 303 may include a sealing protrusion 3030 and a coupling protrusion 3031.

The sealing protrusion 3030 may be formed to correspond to the shapes of the micro-channel 302 and the blood tubes 301 and may be inserted downward into the micro-channel 302 and the blood tubes 301.

In addition, the sealing protrusion 3030 may have a height shorter than the depth of the micro-channel 302. When coupled, as illustrated in FIG. 18, a separation space may be provided so that the blood injected into the blood tubes 301 may flow along the micro-channel 302.

The coupling protrusion 3031 may be inserted into and coupled to the first coupling groove 3000 and the second coupling groove 3001 of the kit body 300.

Specifically, the coupling protrusion 3031 may include a first coupling protrusion 3031$a$ and a second coupling protrusion 3031$b$.

The first coupling protrusion 3031$a$ may be formed to protrude upward along the outer circumferential surface of the upper surface of the micro-channel cover 303. Accordingly, the first coupling protrusion 3031$a$ may be inserted into the first coupling groove 3000 of the kit body 300 so that the kit body 300 and the micro-channel cover 303 may be coupled to each other.

The second coupling protrusion 3031$b$ makes the coupling between the micro-channel cover 303 and the kit body 300 more firmly. The second coupling protrusion 3031$b$ may be formed adjacent to the first coupling protrusion 3031$a$. A plurality of second coupling protrusions 3031$b$ may be formed in a zigzag manner in the front and rear directions along the longitudinal direction and may be inserted into the second coupling grooves 3001.

In addition, the upper surface of the second coupling protrusion 3031$b$ may be inclined downward from the outside to the inside. Accordingly, as the second coupling protrusion 3031$b$ is inserted into the second coupling groove 3001, the coupling force may be improved and the micro-channel cover 303 may be easily removed during separation.

When the injection cover 304 is inserted into the cover insertion groove 3010 formed on the upper side of the blood tubes 301 and blood is injected into the blood tubes 301 with the pipette unit 81, it is possible to prevent bubbles from being formed in the blood by preventing outside air from being injected together with the blood. Accordingly, it is possible to prevent the flow of blood from being hindered by air bubbles in the blood.

The injection cover 304 may include a blood injection hole 3040 and a friction protrusion 3041.

Referring to FIG. 19, the blood injection hole 3040 may be formed to penetrate from the upper surface to the lower surface of the injection cover 304 and may include an upper injection hole 3040$a$ and a lower injection hole 3040$b$.

The upper injection hole 3040$a$ may be formed on the upper side of the injection cover 304, and may have a diameter gradually narrowing from the upper end to the lower end. That is, the upper injection hole 3040$a$ may be formed so that the upper portion is wide and the lower portion is narrow. Accordingly, when blood is injected into the pipette unit 81, the inclined structure of the pipette unit 81 and the upper injection hole 3040$a$ are precisely matched, and thus, blood can be injected while the pipette unit 81 and the upper injection hole 3040$a$ are in close contact with each other, thereby preventing outside air from being introduced together.

The lower injection hole 3040$b$ may be formed on the lower side of the injection cover 304, and may have a diameter gradually narrowing from the lower end to the upper end. That is, the lower injection hole 3040$b$ may be formed so that the upper portion is narrow and the lower portion is wide.

The lower injection hole 3040$b$ and the upper injection hole 3040$a$ may be directly connected to each other, but may also be connected by a middle injection hole. The middle injection hole may have the same diameter from the upper end to the lower end to connect the lower injection hole 3040$b$ and the upper injection hole 3040$a$. In this case, the introduction of outside air may be more effectively blocked by making the end portion of the inclined structure of the pipette unit 81 come into close contact.

In addition, the lower injection hole 3040$b$ may have a larger diameter than the upper injection hole 3040$a$.

When the lower injection hole 3040$b$ is formed as described above and blood is injected through the pipette unit 81, if even a little outside air is introduced together, the introduced air may stay in the lower injection hole 3040$b$ without introducing the micro-channel 302 along with the blood.

Accordingly, it is possible to effectively prevent formation of air bubbles in the blood.

The friction protrusion 3041 may be formed to protrude along the outer circumferential surface of the injection cover 304, and may be fixed more firmly by friction when the injection cover 304 is inserted into the cover insertion groove 3010, thereby preventing outside air from being introduced.

On the other hand, the blood injection hole 3040 of the injection cover 304 is not limited to the above shape and may be formed in other shapes. This will be described as an example with reference to FIG. 20.

As illustrated in FIG. 20($a$), the blood injection hole 3040 of the injection cover 304 may be formed to have a diameter narrowing from the upper end to the lower end, and may be formed so that the inclination has a left-right asymmetrical shape. That is, the left inclination may be greater than the right inclination.

The lower injection hole 3040$b$ may be formed to be connected to the lower end of the upper injection hole 3040$a$, and may have the same diameter from the upper end to the lower end.

Accordingly, when blood is injected into the blood injection hole 3040 through the pipette unit 81, the blood flows along one side wall of the blood tubes 301. Therefore, it is possible to prevent blood from splashing inside the blood tubes 301, thereby preventing the blood viscosity measurement accuracy from deteriorating.

As illustrated in FIG. 20(*b*), the blood injection hole 3040 of the injection cover 304 may be formed to have a diameter narrowing from the upper end to the lower end.

At this time, the blood injection hole 3040 may be formed so that the inclination is left-right symmetrical in cross-section, but the present invention is not limited thereto, and the blood injection hole 3040 may also be formed so that the inclination has a left-right asymmetrical shape. In this case, when blood is injected into the blood injection hole 3040 through the pipette unit 81, blood may be injected along the walls of the blood tubes 301. Therefore, viscosity measurement errors may be reduced by minimizing a phenomenon in which blood splashes due to collision with walls inside the blood tubes 301.

As illustrated in FIG. 20(*c*), the blood injection hole 3040 of the injection cover 304 may be formed to have a diameter narrowing from the lower end to the upper end.

As illustrated in FIG. 20(*d*), the blood injection hole 3040 of the injection cover 304 may be formed to have the same diameter from the upper end to the lower end. In this case, the diameter of the blood injection hole 3040 may be smaller than the largest diameter of the pipette tip of the pipette unit 81. Accordingly, when blood is injected, the upper side of the blood injection hole 3040 may be sealed by the pipette tip, so that the introduction of outside air may be blocked.

In addition, the blood injection hole 3040 may be formed in the center or on one side of the injection cover 304 so that one wall of the blood injection hole 3040 corresponds to the position of one wall of the blood tubes 301.

As described above, when the blood injection hole 3040 is formed on one side of the injection cover 304, blood may be injected along the walls of the blood tubes 301. Therefore, it is possible to minimize a phenomenon in which blood splashes inside the blood tubes 301.

As described above, the multi-channel blood viscosity measuring device according to an embodiment of the present invention is capable of automatically measuring the viscosity of the blood sample accommodated in the blood collection tube without a separate operation by the device operator and discarding a waste kit after measuring the blood viscosity, whereby it may be efficient when blood samples are measured in large quantities.

In addition, since the viscosity of each blood sample is uniformly measured, the accuracy of measuring the viscosity of each blood sample may be improved.

In addition, since the viscosity measurement of one or more blood samples may be performed simultaneously, the work time may be further shortened.

Although the embodiments of the present invention have been described with reference to the accompanying drawings, those of ordinary skill in the art to which the present invention pertains will understand that the present invention may be embodied in other specific forms without changing the technical spirit or essential features. Therefore, it will be understood that the embodiments described above are illustrative in all aspects and are not restrictive.

The invention claimed is:

1. A multi-channel blood viscosity measuring device comprising:

a blood sample mounting tray with a plurality of blood collection tube mounting holes arranged in a two-dimensional array configured to mount a plurality of blood collection tubes;

a blood sample preprocessor having:

a blood collection tube detector having a laser or image scanner configured to generate blood collection tube mounting information including coordinates of locations and number of the plurality of blood collection tubes, at least one preprocessing clamp assembly, and a preprocessing position adjuster having a plurality of preprocessing actuators to move the at least one preprocessing clamp assembly in three (3) axis directions;

a blood sample transferor, wherein the at least one preprocessing clamp assembly is configured to automatically pick up the plurality of blood collection tubes randomly placed on the blood sample mounting tray based on detected coordinates in an operator-free manner, and transfer the plurality of blood collection tubes to the blood sample transferor;

a blood viscosity measurer having a plurality of channels, each of the plurality of the channels having a separate viscosity analyzer receiving a blood viscosity measuring kit, wherein the blood viscosity measurer measures a viscosity of a plurality of blood samples injected into the respective blood viscosity measuring kits from the plurality of blood collection tubes, simultaneously; and a blood sample post-processor configured to mount the blood viscosity measuring kit including a micro-channel assembly on the blood viscosity measurer, suction a blood sample from the blood collection tube, and inject the blood sample into the mounted blood viscosity measuring kit including the micro-channel assembly.

2. The multi-channel blood viscosity measuring device of claim 1, wherein the at least one preprocessing clamp assembly includes:

a preprocessing clamp holding or placing the blood collection tube, a first rotator rotating the preprocessing clamp around z-axis, and a second rotator rotating the preprocessing clamp around x-axis or y-axis.

3. The multi-channel blood viscosity measuring device of claim 1, wherein the plurality of the preprocessing actuators include:

a preprocessing up-and-down adjuster adjusting a position of the at least one preprocessing clamp assembly in an up-and-down direction, a preprocessing left-and-right adjuster adjusting the position of the at least one preprocessing clamp assembly in a left-and-right direction, and a preprocessing front-and-rear adjuster adjusting the position of the at least one preprocessing clamp assembly in a front and rear direction.

4. The multi-channel blood viscosity measuring device of claim 1, wherein the blood sample transferor includes:

a transfer clamp assembly on which the blood collection tube is placed by the blood sample preprocessor, and a transfer actuator connected to the transfer clamp assembly to transfer the placed blood collection tube.

5. The multi-channel blood viscosity measuring device of claim 1, wherein the each of the plurality of the channels further includes:

a kit mounter on which the blood viscosity measuring kit is mounted and a kit inserter inserting or withdrawing the kit mounter into or from the viscosity analyzer.

6. The multi-channel blood viscosity measuring device of claim 1, wherein the blood sample post-processor has a plurality of post-processing adjusters, which include:

a post-processing up-and-down adjuster adjusting positions of at least one kit clamp and at least one pipette body in an up-and-down direction, a post-processing left-and-right adjuster adjusting the position of the at least one kit clamp and the at least one pipette body in a left-and-right direction, and a post-processing front-and-rear adjuster adjusting the positions of the at least one kit clamp and the at least one pipette body in a front and rear direction.

7. The multi-channel blood viscosity measuring device of claim 6, wherein the post-processing up-and-down adjuster includes a dual adjuster structure having:

a kit up-and-down adjuster configured to independently adjust a vertical position of the at least one kit clamp; and an integrated up-and-down adjuster connected to both the kit up-and-down adjuster and the at least one pipette body to simultaneously translate vertical positions of the at least one kit clamp and the at least one pipette body while maintaining a predetermined safety gap therebetween.

8. The multi-channel blood viscosity measuring device of claim 1, further comprising:

a controller for controlling operations of the blood sample preprocessor, the blood sample transferor, the blood viscosity measurer, and the blood sample post-processor, and a monitor monitoring a viscosity measurement result measured by the blood viscosity measurer.

9. The multi-channel blood viscosity measuring device of claim 1, further comprising a blood viscosity measurement cartridge for storing the blood viscosity measuring kit before use.

10. The multi-channel blood viscosity measuring device of claim 1, further comprising a waste processor accommodating the blood viscosity measuring kit for which the viscosity measurement of the blood sample has been completed in the blood viscosity measurer.

11. The multi-channel blood viscosity measuring device of claim 1, wherein the micro-channel assembly includes a wave-shaped micro-channel formed by a plurality of first bent portions and second bent portions alternating in a forward and backward direction, wherein the wave-shaped micro-channel has a predetermined number or width of the plurality of first bent portions and second bent portions.

12. The multi-channel blood viscosity measuring device of claim 1, wherein the two-dimensional array comprises a grid of rows and columns of the blood collection tube mounting holes.

13. The multi-channel blood viscosity measuring device of claim 2, wherein the preprocessing clamp includes at least a pair of clamps, each of the at least a pair of clamps having a gripping groove on an inner surface thereof and a hooking portion protruding from one end of the gripping groove.

14. The multi-channel blood viscosity measuring device of claim 3, wherein the preprocessing up-and-down adjuster includes a first up-and-down connecting arm connected to the at least one preprocessing clamp assembly, and a first up-and-down adjusting actuator connected to the first up-and-down connecting arm to move the first up-and-down connecting arm in the up-and-down direction;

the preprocessing left-and-right adjuster includes a first left-and-right connecting arm connected to the first up-and-down adjusting actuator, and a first left-and-right adjusting actuator connected to the first left-and-right connecting arm to move the first left-and-right connecting arm in the left-and-right direction; and the preprocessing front-and-rear adjuster includes a first front-and-rear connecting arm connected to the first left-and-right adjusting actuator, and a first front-and-rear adjusting actuator connected to the first front-and-rear connecting arm to move the first front-and-rear connecting arm in the front-and-rear direction.

15. The multi-channel blood viscosity measuring device of claim 6, wherein the post-processing left-and-right adjuster includes a second left-and-right connecting arm connected to the post-processing up-and-down adjuster, and a second left-and-right adjusting actuator connected to the second left-and-right connecting arm to move the second left-and-right connecting arm in the left-and-right direction; and the post-processing front-and-rear adjuster includes a second front-and-rear connecting arm connected to the post-processing left-and-right adjuster, and a second front-and-rear adjusting actuator connected to the second front-and-rear connecting arm to move the second front-and-rear connecting arm in the front-and-rear direction.

16. The multi-channel blood viscosity measuring device of claim 7, wherein the kit up-and-down adjuster includes a kit up-and-down connecting arm connected to the at least one kit clamp, and a kit up-and-down adjusting actuator connected to the kit up-and-down connecting arm to move the kit up-and-down connecting arm in the up-and-down direction; and the integrated up-and-down adjuster includes an integrated up-and-down connecting arm connected to the kit up-and-down adjusting actuator and the at least one pipette body, and an integrated up-and-down adjusting actuator connected to the integrated up-and-down connecting arm to move the integrated up-and-down connecting arm in the up-and-down direction.

17. The multi-channel blood viscosity measuring device of claim 7, wherein the kit up-and-down adjuster and the integrated up-and-down adjuster have different lengths.

18. The multi-channel blood viscosity measuring device of claim 1, wherein a processor controls gripping and hooking of a blood collection tube cover, transfer of the blood collection tube, insertion of the blood viscosity measuring kit into the viscosity analyzer, adjustment of the at least one kit clamp and at least one pipette body, suction and injection of the blood sample, and determination of a number of repetitions for viscosity measurements based on a number of the plurality of blood collection tubes mounted on the blood sample mounting tray.

19. The multi-channel blood viscosity measuring device of claim 1, wherein the viscosity analyzer includes an optical sensor to detect blood height changes in the blood viscosity measuring kit.

20. The multi-channel blood viscosity measuring device of claim 5, wherein each of the plurality of the channels further includes a guide rail and the kit inserter having a kit inserter cylinder connected to the guide rail, the kit inserter cylinder extending horizontally to insert or withdraw the kit mounter into or from the viscosity analyzer.

* * * * *